(12) United States Patent
Ambrosio et al.

(10) Patent No.: US 10,525,161 B2
(45) Date of Patent: Jan. 7, 2020

(54) BIOCOMPOSITE OF BIOMINERALIZED GRAPHENE OXIDE AND ITS USE FOR BONE TISSUE ENGINEERING

(71) Applicants: CONSIGLIO NAZIONALE DELLE RICERCHE, Rome (IT); JOINTHERAPEUTICS S.R.L., Como (IT)

(72) Inventors: Luigi Ambrosio, Rome (IT); Maria Grazia Raucci, Rome (IT); Angela Longo, Rome (IT); Gianfranco Carotenuto, Rome (IT); Daniela Giugliano, Rome (IT)

(73) Assignees: CONSIGLIO NAZIONALE DELLE RICERCHE, Rome (IT); JOINTHERAPEUTICS S.R.L., Como (IT)

(*) Notice: Subject to any disclaimer, the term of this patent is extended or adjusted under 35 U.S.C. 154(b) by 49 days.

(21) Appl. No.: 15/747,895

(22) PCT Filed: Jul. 26, 2016

(86) PCT No.: PCT/IB2016/054459
§ 371 (c)(1),
(2) Date: Jan. 26, 2018

(87) PCT Pub. No.: WO2017/017610
PCT Pub. Date: Feb. 2, 2017

(65) Prior Publication Data
US 2018/0214599 A1    Aug. 2, 2018

(30) Foreign Application Priority Data

Jul. 29, 2015  (IT) .................. 102015000039459

(51) Int. Cl.
*A61L 27/08* (2006.01)
*A61L 27/12* (2006.01)

(52) U.S. Cl.
CPC ............ *A61L 27/08* (2013.01); *A61L 27/12* (2013.01); *A61L 2420/04* (2013.01); *A61L 2430/02* (2013.01)

(58) Field of Classification Search
CPC ................... A61L 27/08; A61L 27/12
See application file for complete search history.

(56) References Cited

U.S. PATENT DOCUMENTS 6,153,266 A    11/2000  Yokogawa et al.

FOREIGN PATENT DOCUMENTS

WO    1997017285 A1    5/1997
WO    2009088519 A1    7/2009

OTHER PUBLICATIONS

International Search Report of PCT/IB2016/054459 dated Oct. 10, 2016.

(Continued)

*Primary Examiner* — Jason-Dennis N Stewart
(74) *Attorney, Agent, or Firm* — Silvia Salvadori, P.C.; Silvia Salvadori

(57) ABSTRACT

It is disclosed a biocomposite of hydroxyapatite on graphene oxide sheets and its use for bone tissue engineering applications, such as bone repair, bone augmentation, as well as coating of biomedical implants. Processes for preparing said biocomposites are also described.

14 Claims, 16 Drawing Sheets

(56) References Cited

OTHER PUBLICATIONS

Li M. et al., "Graphene oxide/hydroxyapatite composite coatings fabricated by electrophoretic nanotechnology for biological applications", Carbon, vol. 67, Dec. 31, 2014, pp. 185-197.
Sungjin K, et al., "Graphene-biomineral hybrid materials", Advanced Materials, vol. 23, No. 17, May 3, 2011, pp. 2009-2014.
Written Opinion of PCT/IB2016/054459 dated Oct. 10, 2016.

*HAGO1%_afterHCl; + HAGO1.5%_afterHCl; # HAGO2%_afterHCl; ** GO

BIOCOMPOSITE OF BIOMINERALIZED GRAPHENE OXIDE AND ITS USE FOR BONE TISSUE ENGINEERING

This application is a U.S. national stage of PCT/IB2016/054459 filed on 26 Jul. 2016, which claims priority to and the benefit of Italian Application No. 102015000039459 filed on 29 Jul. 2015, the contents of which are incorporated herein by reference in their entireties.

FIELD OF THE INVENTION

The present invention concerns a biocomposite of biomineralized graphene oxide and its use for bone tissue engineering applications, such as bone repair, bone augmentation, as well as coating of biomedical implants.

The invention also relates to processes for preparing the biocomposite.

STATE OF THE ART

The development of new biocompatible materials to be used in medicine has acquired a great deal of importance in material science. The main component of natural bone tissues is represented by Hydroxyapatite [$Ca_{10}(PO_4)_6(OH)_2$, shortly 'HA'] that is known to show good biocompatible and bioactive properties with human tissues. Consequently, it is currently widely used in various forms and shapes in bone and tissue engineering. However, the limited mechanical properties of bioceramics in terms of tensile strength and fracture toughness compared with natural bone limit its applications for replacing various parts of the bone systems.

To resolve this problem, composite materials based on polyethylene, polycaprolactone, $Al_2O_3$, $TiO_2$, zirconia ($ZrO_2$) and carbon nanotubes (CNT) with HA were prepared by different approaches including aqueous colloidal precipitation, sol-gel and mechano-chemical methods. Although increased mechanical properties have been obtained, these reinforcements, e.g. CNT, due to the presence of metallic catalyst therein, could usually impair the biological property of HA or have adverse effects on adjacent tissues. Some reinforcing material (e.g., $ZrO_2$) could induce the decomposition of HA during the fabrication process, leading to a substantially reduction in the bioactivity of HA. Conversely, an ideal reinforcement material should impart mechanical integrity to the composite without diminishing its bioactivity.

It is therefore an object of the present invention to provide a biomaterial, which overcomes the drawbacks of those known in the art.

SUMMARY OF THE INVENTION

The above object has been achieved by a biocomposite of hydroxyapatite (shortly 'HA') on graphene oxide (shortly 'GO') sheets, as reported in claim 1.

Hydroxyapatite is a calcium phosphate which is commonly denoted as $Ca_5(PO_4)_3(OH)$, therefore belonging to the apatite group and containing an $OH^-$ group. For the purposes of the present invention, the term "hydroxyapatite" also encompasses, in addition to the aforesaid, all polymorphic forms, relative hydrates and solvates, in all ratios between phosphate ions, hydroxyl ions and calcium, as well as all hydroxyapatite precursors, such as amorphous calcium phosphate (ACP), octacalcium phosphate (OCP), and calcium phosphate in all polymorphic forms, relative hydrates and solvates, in all ratios between phosphate ions, hydroxyl ions and calcium.

In a further aspect, the present invention concerns a first process for preparing said biocomposite.

In another aspect, the present invention concerns a biocomposite obtainable by said first process, wherein hydroxyapatite is in the form of spindle-like nanoparticles intercalated among graphene oxide sheets.

In an additional aspect, the present invention concerns the use of a second process for preparing said biocomposite.

In another aspect, the present invention concerns a biocomposite obtainable by said second process and comprising amorphous calcium phosphate on graphene oxide sheets.

In an even further aspect, the present invention concerns the use of the biocomposite for coating biomedical implants.

BRIEF DESCRIPTION OF THE FIGURES

The characteristics and the advantages of the present invention will become apparent from the following detailed description, from the working examples provided for illustrative purposes, and from the annexed Figures wherein.

DETAILED DESCRIPTION OF THE INVENTION

Figure 1:
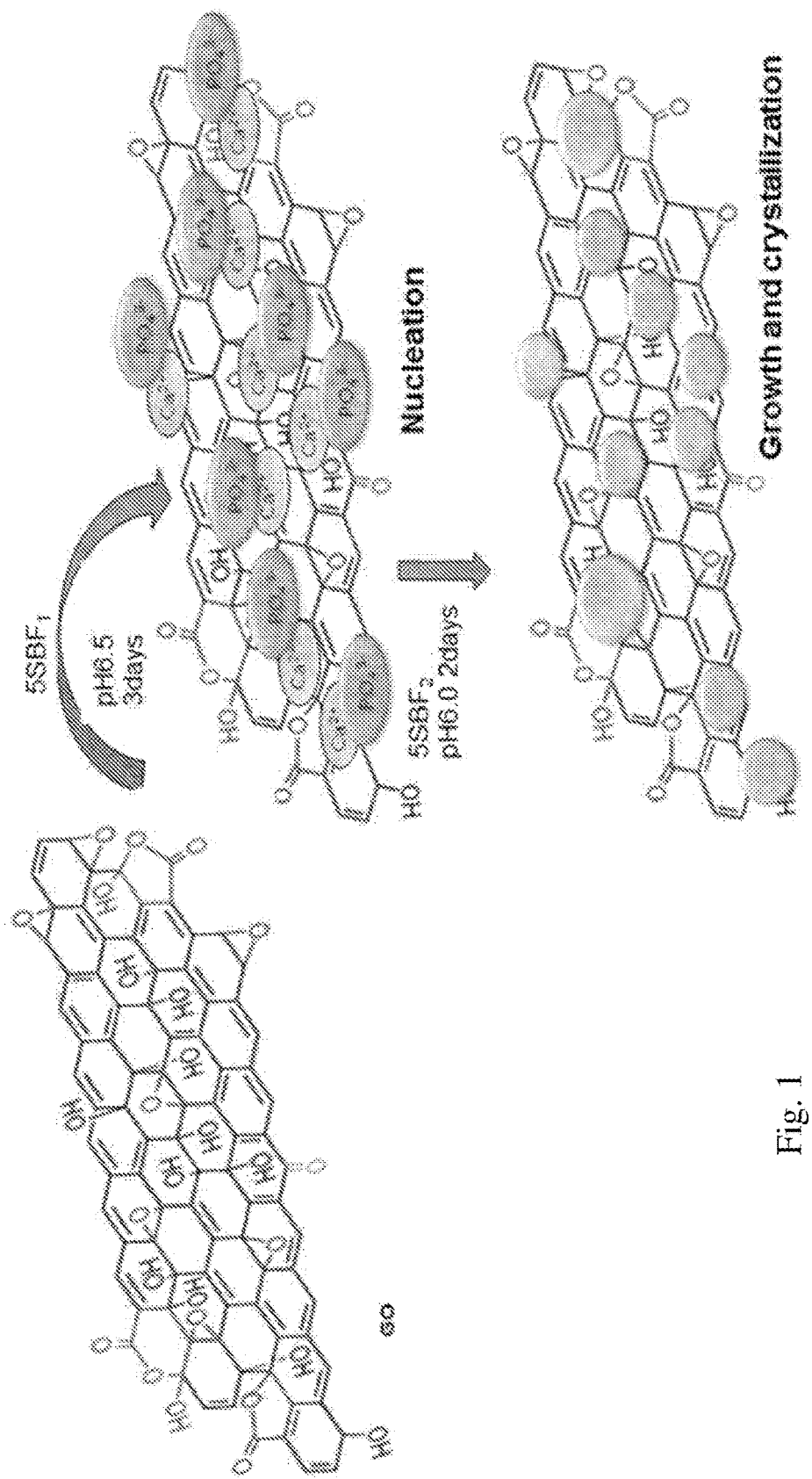
FIG. 1: Mechanism of biomimetic preparation of biomineralized GO material.

The subject of the invention therefore is a biocomposite of hydroxyapatite on graphene oxide sheets.

Preferably, the amount of graphene oxide is 0.5-3.0 wt % on the weight of the biocomposite.

Preferably, the biocomposite further comprises calcium phosphate on graphene oxide sheets. The presence of calcium phosphate on graphene oxide sheets improves the bioactivity and cellular recognition.

In a further aspect, the invention concerns a first process for preparing said biocomposite, the process comprising the steps of:

i) providing and sonicating an aqueous solution of graphene oxide to exfoliate graphene oxide sheets, ii) providing an aqueous solution of a Calcium salt selected from nitrate, sulphate, hydrogen sulphate, carbonate, chloride, nitride, and combinations thereof, iii) adding the aqueous solution of step ii) to the aqueous solution of step i), iv) providing an aqueous solution of a phosphorus salt selected from dihydrogen phosphate, hydrogen phosphate, phosphate, dihydrogen phosphite, hydrogen phosphite, phosphite, and combinations thereof, and v) adding the aqueous solution of step iv) to aqueous solution obtained in step iii), and gelating by adjusting to alkaline pH, thus obtaining the biocomposite.

In step i), an aqueous solution of graphene oxide is provided.

Graphene oxide can be synthesized from Graphene Nanoplatelets (GNP) using a modified and simplified Hummers' method (Park S. et al., 2008, *Aqueous suspension and characterization of chemically modified graphene sheets*, Chem Mater, 20:6592-6594).

In preferred embodiments, graphene oxide is obtained by oxidation of GNP with $H_2SO_4$ $KNO_3$ and $KMnO_4$. Typically, a mixture of GNP and $KNO_3$ in $H_2SO_4$ is stirred for few min in an ice bath. After that, $KMnO_4$ is added slowly with stirring in small portions to prevent temperature rise in excess of 20° C. Then, the temperature of the reaction mixture is raised to 35° C. and stirred. After completion of the reaction, water is gradually added into the solution. The resulting suspension is reacted further by adding a mixture of $H_2O_2$ and water. During oxidation, the color of the mixture turns from dark purplish-green to dark brown. To stop the oxidation process, $H_2O_2$ solution is added and the color of the mixture turns to bright yellow, thus indicating a high oxidation level of graphite. The GO is separated from the reaction mixture by filtration and successively washed with water until a pH of 4-5 is achieved. The washing process can be carried out by using a simple decantation of the supernatant with a centrifugation technique. During the washing process, the graphite oxide undergo exfoliation, which resulted in thickening of the graphene oxide solution, forming graphene oxide gel which is used to obtain the graphene oxide solid.

Preferably, in the aqueous solution of step i), graphene oxide is in a concentration of 0.005 g/mL-0.01 g/mL.

In step i), the aqueous solution of graphene oxide is then sonicated to exfoliate graphene oxide sheets.

Preferably, the sonication is carried out at room temperature for at least 2 hours.

In preferred embodiments, the sonication is carried out at room temperature for at least 6 hours.

In step ii), an aqueous solution of a Calcium salt is provided, said Calcium salt being selected from nitrate, sulphate, hydrogen sulphate, carbonate, chloride, nitride, and combinations thereof.

In preferred embodiments, the Calcium salt is Calcium nitrate.

In step iii), the aqueous solution of step ii) is added to the aqueous solution of step i).

Preferably, the aqueous solution obtained in step iii) is ultrasonicated at room temperature for at least 20 minutes.

In preferred embodiments, the aqueous solution obtained in step iii) is ultrasonicated at room temperature for 25-45 minutes.

In step iv), an aqueous solution of a phosphorus salt is provided, said phosphorus salt being selected from dihydrogen phosphate, hydrogen phosphate, phosphate, dihydrogen phosphite, hydrogen phosphite, phosphite, and combinations thereof.

Suitable cations of said phosphorus salt are alkali metals, alkaline earth metals and ammonium.

In step v), the aqueous solution of step iv) is added to aqueous solution obtained in step iii), and gelated by adjusting to alkaline pH.

Preferably, in the aqueous solution obtained in step v), the molar ratio between calcium and phosphorus is 1.0 to 3.0, more preferably is 1.2 to 2.0.

Preferably, the pH is adjusted to equal to or higher than 10.

In preferred embodiments, the pH is adjusted to about 11.

In other preferred embodiments, the pH is adjusted by adding ammonium hydroxide.

Preferably, after the adjustment to alkaline pH in step v), the aqueous solution is stirred at room temperature for at least 1 hour.

In preferred embodiments, after the adjustment to alkaline pH in step v), the aqueous solution is stirred at room temperature for about 2 hours.

Preferably, the process further comprises a step vi) of aging the biocomposite obtained in step v) for at least one day at a temperature of at least 50° C., preferably for about two days at a temperature of about 60° C.

Optionally, the resulting biocomposite can be sterilized.

The sterilization can be performed by using ethanol, a solution of ampicillin and streptomycin, or a combination thereof, for 2-6 hours.

In an additional aspect, the present invention concerns a biocomposite of hydroxyapatite on graphene oxide sheets, obtainable by the first process as above described, wherein hydroxyapatite is in the form of spindle-like nanocrystals intercalated among graphene oxide sheets.

Preferably, in the spindle-like nanocrystals of hydroxyapatite, the ratio between calcium and phosphorus is 1.60 to 1.70.

The HA spindle-like nanocrystals so obtained, preferably at room temperature without further treatments, are in a typical shape with a diameter of about 5±0.37 nm and a length of around 70±2.5 nm on the GO sheets.

In preferred embodiments, calcium phosphate is also present on graphene oxide sheets.

The calcium phosphate obtained by said 'sol-gel' first process combines hydroxyapatite (HA) with other calcium phosphate phases, such as dicalcium phosphate (DCP), a precursor of natural HA in bone. As sintered HA has a relatively slow rate of resorption in vivo, however dicalcium phosphate (DCP) and dicalcium phosphate dehydrated (DCPD) offer a valid alternative as their ascertained osteoconductivity is associated with a relatively more rapid resorption rate. At the same time, the presence of GO allows a good distribution of calcium phosphate nanoparticles, thus improving the bioactivity.

Preferably, the biocomposite obtainable by said first process has an X-ray diffraction pattern comprising the following peaks (2θ values): 25.9°, 28.9°, 31.8°, 39.8°, 46.7°, 49.5° and 53.2°.

More preferably, said X-ray diffraction pattern further comprises the following peaks (2θ values): 21.2°, 23.2° and 34.5°.

With respect to said first process of preparation of a biocomposite, it should be acknowledged that a sol-gel approach is adopted, which advantageously allows to achieve a gelation at room temperature and within a conveniently short period of time. In fact, it has been observed that different amounts of graphene oxide (such as 1-1.5-2% wt) delays the gelification time only for few minutes.

It should be also appreciated that, in said first process, no other additives or components (such as silicate, chitosan, etc.) are used to activate or exfoliate GO. The water is preferably the only solvent used.

In preferred embodiments, only the salts of Calcium and phosphorus are used, and ammonium hydroxide as a pH adjuster.

As will be further described in the following Examples, the HA-GO samples were ultrasonically treated before TEM observation. It was observed that almost no HA particles are scattered out of the matrix, thus demonstrating a strong interaction between the HA particles and the GO sheets. The high specific surface area of GO is also beneficial for high loading levels of the HA particles and is helpful for forming an effective network within the biocomposite.

The resulting biocomposite is fully injectable, without phase separation phenomena and agglomeration of inorganic phase, so that it can be advantageously used in minimally invasive surgery.

Moreover, the resulting biocomposite shows good biological properties in terms of proliferation and early osteogenic differentiation of human Mesenchymal Stem Cells, in experiments performed in basal medium without osteogenic factor. In fact, it is possible to observe the increasing Alkaline Phosphatase value with the increasing amount of GO in composite materials.

Said first process can be seen as an in situ synthesis of HA-GO based on a simple mechanism where the oxygen-containing functional groups (such as hydroxyl and carboxyl groups) present on the basal plane and edges of the GO sheets may play an essential role in anchoring calcium ions. A good nucleation of HA nanoparticles on GO sheets is obtained when in situ preparation is performed at high pH value (pH>10) followed by an aging step of 2 days at 60° C. The high pH value promotes the deprotonation of carboxyl groups (—COOH) on the GO sheets and make GO more charged and hydrophilic, which in turn might enhances the interaction between the GO substrates and HA nanoparticles. Moreover, the high pH value (pH>10) and the reaction temperature play important roles in the degree of crystallinity, as well as the phase formation and morphology of HA as demonstrated by TEM investigation. Furthermore, during the synthesis process when the Ca solution is added into the GO solution, the $Ca^{2+}$ cations would be attracted and anchored on the oxygen atoms through electrostatic interactions and functioned as the nuclei for the crystallization and growth of the HA particles. The $Ca^{2+}$ could react in situ with the ambient dropwise phosphate ions via electrovalent bonds to form HA nanoparticles. The high specific surface area of GO is also beneficial for high loading levels of the HA particles and is helpful for forming an effective network inside the biocomposite.

In a further aspect, the invention concerns a second process for preparing said biocomposite, the process comprising the steps of:
a) providing a first supersaturated SBF solution having pH of about 6.5,
b) soaking graphene oxide sheets into said first supersatured SBF solution for a period of 65 to 85 hours,
c) providing a second supersaturated SBF solution having pH of about 6.0,
d) soaking graphene oxide sheets obtained from step b) into said second supersaturated SBF solution for a period of 40 to 60 hours, and
e) rinsing with water and drying the biocomposite.

Preferably, both said first supersaturated SBF solution and said second supersaturated SBF solution are at a temperature of 30 to 40° C., more preferably about 37° C.

In preferred embodiments, both said first supersatured SBF solution and said second supersaturated SBF solution are buffered with Tris-hydroxymethylaminomethane-chloric acid (Trizma-HCl).

In preferred embodiments, the volumes of said first supersatured SBF solution ($5 \times SBF_1$) have been calculated with respect to the total GO surface by using an exposed surface to SBF volume ratio equal to 10 $mm^2$/ml, as reported in literature (Tanahashi M, et al. in: Yamamuro T, Kokubo T, Nakamuro T. Eds. Bioceramics, vol.5, Kobunshi Kankokai, Kyoto, 1992, p. 57.).

It should be appreciated that no preliminary treatment of GO is performed before the SBF treatment steps.

In this second process, biomineralized graphene oxide film is prepared by using Simulated Body Fluid solutions. The SBF treatment is performed on GO film obtained by solvent casting process.

In an additional aspect, the present invention concerns a biocomposite of hydroxyapatite on graphene oxide sheets, obtainable by the second process as above described, wherein said biocomposite comprises amorphous calcium phosphate on graphene oxide sheets.

This second process can be considered a biomimetic method, wherein mineralization is induced by soaking graphene oxide sheets in a supersaturated 5×SBF solution. In fact, the presence of anionic functional groups in GO facilitates, in the first step of treatment, the nucleation of biominerals by attracting more $Ca^{2+}$ cations to deposit onto film surface and subsequently forming biominerals with $PO_4^{3-}$. The second step of treatment concerns the growth and crystallization of apatite in a $Mg^{2+}$ and $HCO_3^-$ free 5×SBF solution. The nucleation of HA on the bioinspired surface is monitored by physical-chemical and morphology analysis. In the following Examples, it will be seen that a deposition of amorphous calcium phosphate (ACP) occurs. ACP is often encountered as a transient phase during the formation of calcium phosphates in aqueous systems. Usually, ACP is the first phase that is precipitated from a supersaturated solution prepared by rapid mixing of solutions containing of calcium cations and phosphate anions. ACP is also treated as a precursor of biological apatite during bone formation.

Preferably, this second process further comprises a step f) of aging the biocomposite obtained in step e) for at least one day at a temperature of at least 50° C., preferably for about two days at a temperature of about 60° C.

It was found that in the biocomposites obtained by the first process (sol-gel approach), the spindle-like hydroxyapatite nanoparticles were present randomly and strongly on the surface. The oxygen-containing functional groups, such as hydroxyl and carbonyl groups, present on the basal plane and edges of the GO sheets play an important role in anchoring calcium ions as demonstrated by FTIR and TEM investigations. A different result was obtained for biocomposites obtained by the second process (biomimetic approach): an amorphous calcium phosphate on GO sheet was observed after 5 days of treatment. These different approaches resulted in a diverse effect on proliferation and osteogenic mesenchymal stem cells differentiation. In fact, in the biocomposites prepared by sol-gel approach the expression of early marker of osteogenic differentiation, i.e. ALP, increases along with the amount of GO in the first days of cell culture. Meanwhile, biomimetic materials sustain the cell viability and proliferation, even if the expression of alkaline phosphatase activity in a basal medium is delayed. Consequently, the biocomposites of the invention can be used in bone repair, bone augmentation, as well as coating of biomedical implants. In fact, in a further aspect, the present invention concerns the use of the biocomposite, as above described for coating biomedical implants.

The effect of the step of aging the biocomposite obtained either by the first process or by the second process has been also further investigated, as well reported and discussed in Example 4.

It has been observed that an intense aging promotes the conversion of graphene oxide into graphene, thus further improving the properties and performances of the biocomposite.

Therefore, in preferred embodiments, the biocomposite comprises hydroxyapatite on graphene oxide sheets and graphene sheets.

Preferably, in this biocomposite, the conversion degree of the graphene oxide into graphene is higher than 90%, preferably higher than 95%.

It should be understood that all aspects identified as preferred and advantageous for the biocomposite of the invention are to be deemed as similarly preferred and advantageous also for the first process, the second process, the biocomposites obtainable thereby, as well as the use for coating biomedical implants.

It should be also understood that all the combinations of preferred aspects of the biocomposite, the first process, the second process, the biocomposites obtainable thereby, and the use for coating biomedical implants, as above reported, are to be deemed as hereby disclosed.

Below are working examples of the present invention provided for illustrative purposes.

EXAMPLES

Example 1

Synthesis of GO

Graphene oxide was synthesized from Graphene Nanoplatelets (GNP) using a modified and simplified Hummers' method (Park S. et al., 2008, *Aqueous suspension and characterization of chemically modified graphene sheets*, Chem Mater, 20:6592-6594). In particular, this material was obtained by oxidation of 0.5 g of GNP with 25 mL of $H_2SO_4$ (sulfuric acid 99.999%, Aldrich), 1 g of KNO3 (potassium nitrate, Aldrich) and 3 g of $KMnO_4$ (potassium permanganate, Aldrich). Typically, a mixture of GNP and $KNO_3$ in $H_2SO_4$ was stirred for few min below 5° C. in an ice bath. After that, $KMnO_4$ was added slowly with stirring in small portions to prevent temperature rise in excess of 20° C. Then, the temperature of the reaction mixture was raised to 35° C. and the mixture was stirred for 60 mins. After completion of the reaction, 100 mL of deionized water was gradually added into the solution. The suspension was reacted further by adding a mixture of $H_2O_2$ (7 mL, 30%) and water (55 mL). During oxidation, the color of the mixture turned from dark purplish-green to dark brown. To stop the oxidation process, $H_2O_2$ solution was added and the color of the mixture turned to bright yellow, thus indicating a high oxidation level of graphite. The GO was separated from the reaction mixture by filtration and successively was washed five times with deionized water until a pH of 4-5 was achieved. The washing process was carried out using a simple decantation of the supernatant with a centrifugation technique. During the washing process with deionized water, the graphite oxide underwent exfoliation, which resulted in thickening of the graphene oxide solution, forming graphene oxide gel which was used to obtain the graphene oxide solid.

Example 2

In situ Preparation of HA-GO, According to the First Process

HA-GO was synthesized at room temperature with $Ca(NO_3)_2 \cdot 4H_2O$ (99% A.C.S. Reagent, Aldrich) and $(NH_4)H_2PO_4$ (A.C.S. reagent, Aldrich), as Ca and P precursors respectively. The amount of $Ca(NO_3)_2 \cdot 4H_2O$ was chosen to allow a Ca/P ratio equal to 1.67. Commonly, the molar ratio of calcium to phosphorus Ca/P varies from 1.2 to almost 2 in HA and in the stoichiometric HA Ca/P is 1.67. However, this is not the value observed in the organism because small amounts of carbon, nitrogen, iron and other incorporated elements. Meanwhile, the theoretical amount of GO was determined as percentage weight (1.0-1.5-2.0 w/w %) of final product.

In order to perform the synthesis of HA-GO, an exfoliation of graphene was carried out in appropriated amount of distilled water through sonication for several hours at room temperature.

When $Ca(NO_3)_2 \times 4H_2O$ was completely dissolved in distilled water, $Ca^{2+}$ solution (3 M) was added to GO sheet water solution to promote the interaction between ions $Ca^{2+}$ and lateral and superficial groups of GO. A homogeneous $GO/Ca^{2+}$ system was obtained by ultrasonic dispersion for 30 min, after that a phosphorus solution (3.58 M) was added dropwise to the system and pH was adjusted at alkaline value (pH equal to 11) by $NH_4OH$. Gelation took place after 2 hrs of magnetic stirring at room temperature; after that, an aging step of 2 days at 60° C. was performed.

Example 3

Biomimetic Preparation of Biomineralized GO, According to the Second Process

To produce biomineralized products GO sheets a treatment has been carried out, which combines the preliminary use of a supersaturated SBF solution ($5 \times SBF_1$) to stimulate the nuclei formation, while a fresh chemically-modified solution ($5 \times SBF_2$) is further used, in order to promote the growing of apatite nuclei, once formed (FIG. 1). Both solutions were buffered at pH 6.5 and 6 respectively, by using Tris-hydroxymethylaminomethane-chloric acid (Trizma-HCl). The biomimetic treatment consisted of two steps in a pH-controlled environment: during the first step, samples with pre-ordered size were soaked into $5 \times SBF_1$ at pH=6.5 where the $5 \times SBF$ solution volumes have been calculated respect to the total material surface by using an exposed surface to SBF volume ratio equal to 10 mm$^2$/ml, as reported in literature (Tanahashi M, et al. in: Yamamuro T, Kokubo T, Nakamuro T. Eds. Bioceramics, vol. 5, Kobunshi Kankokai, Kyoto, 1992, p. 57). The solution temperature was fixed at 37° C. during the treatment. After the sequential immersion in 5×SBF$_1$ (3 days) and in 5×SBF$_2$ (2 days), all materials were gently rinsed in distilled water to remove excess ions and, then, dried overnight under laminar hood.

Characterization

—Thermogravimetric Analysis

Thermogravimetric analysis (TGA) was performed to evaluate the effective weight percentage of GO in the HA-GO biocomposites using a TA instrument TGA model Q5000IR. Measurement was performed in atmosphere by increasing the temperature from 50 up to 600° C. through at 5° C./min scan.

—X-Ray Diffraction and Infrared Spectroscopy FTIR Analyses

X-ray diffraction (XRD) was implemented to detect phase composition and crystallinity of HA-GO materials by an X-ray diffractometer (XRD-PANalytical X'Pert Pro) from 2Θ=5° to 85° using CuKα radiation. FTIR spectroscopy was performed on Nicolet Nexus spectrophotometer with KBr discs in the 500-4000 cm$^{-1}$ region (4 cm$^{-1}$ resolution, average 64 scans).

—Morphological Characterization

The morphology of the composite materials was characterized by using a Scanning Electron Microscope (SEM) and Transmission Electron Microscope (TEM). For SEM analysis (Quanta200—FEI, the Netherlands), the materials were mounted by a double adhesive tape to aluminum stubs. The stubs were sputter-coated with gold to a thickness of around 20 nm (Emitech Sk500). SEM analysis was performed at different magnification at 20 keV. X-ray energy dispersive spectroscopy (EDAX, Genesis 2000i) analysis was used for a qualitative estimation of the Ca/P ratio.

The Transmission Electron Microscopy (TEM) images were taken by a TEM FEI Tecnai G12 Spirit Twin model instrument operated at an accelerating voltage of 100 kV. Samples for TEM imaging were prepared by placing a drop of the aged HA-GO composite suspensions (the suspensions were diluted in deionized water and dispersed by ultrasonic waves before use) onto carbon coated copper grids, dried in air and loaded into the electron microscope chamber.

—Bioactivity Test

In order to study their bioactivity, samples of HA-GO 1.5 wt % gel material studied was immersed in 2 mL of an acellular simulated body fluid (SBF) with ion concentrations (Na$^+$ 142.0, K$^+$ 5.0, Ca$^{2+}$ 2.5, Mg$^{2+}$ 1.5, Cl$^-$ 147.8, HCO$_3^-$ 4.2, HPO$_4^{2-}$ 1.0, SO$_4^{2-}$ 0.5 mM) nearly equal to those in human blood plasma, at ~4° C. and contained in a polystyrene bottle. The SBF was prepared by dissolving reagent grade chemicals NaCl, NaHCO$_3$, KCl, MgCl$_2$, HCl 1 M, CaCl$_2$.6H$_2$O, Na$_2$SO$_4$, (SigmaAldrich) in ultra-pure water and buffered at pH 7.4 using tris(hydroxymethyl)-aminoethane (SigmaAldrich) and 1M HCl at 37° C. After an immersion period of 7 days, the materials were removed from the SBF, gently washed with ultra-pure water, and dried at 40° C. The ability to form an apatite deposition was studied by submitting reacted samples to SEM investigation.

—Biological Properties

In Vitro Cell Culture

Biological assays were performed using human Mesenchymal Stem Cells line (hMSC) obtained from LONZA (Milano, Italy). hMSC were cultured in 75 cm$^2$ cell culture flask in Eagle's alpha Minimum Essential Medium (α-MEM) supplemented with 10% Fetal Bovine Serum (FBS), antibiotic solution (streptomycin 100 µg/ml and penicillin 100 U/ml, Sigma Chem. Co) and 2 mM L-glutamine, without osteogenic factors. hMSCs from passages 4 through 6 passage were used for all the experimental procedures and incubated at 37° C. in a humidified atmosphere with 5% CO$_2$ and 95% air.

Viability Test

To evaluated cell biocompatibility, hMSC were plated at concentration of 1.6×10$^4$ in triplicate onto HA, GO, GO_SBF and HA-GO materials at different concentrations (1-1.5-2 wt %). The medium in cell-load gel materials culture plates were removed after cultured for 7, 14 and 21 and the in vitro cell viability was checked by the Alamar blue assay (AbD Serotec, Milano, Italy). This assay quantified the redox indicator which changed to a fluorescent product in response to the chemical reduction by mitochondrial enzymes, such as flavin mononucleotide dehydrogenase, flavin adenine dinucleotide dehydrogenase, and nicotinamide adenine dinucleotide dehydrogenase. In addition, a redox phenomenon gave a quantitative indication of metabolic activity of live cells. An aliquot of 1 mL of Alamar Blue™ diluted 1:10 in phenol red-free medium was added to each well and incubated for a further 4 h at 37° C., 5% CO$_2$. Later, 200 µL of this solution was transferred into a 96 well plate for colorimetric analysis. Wells without any cells were used to correct any background interference from the redox indicator. The optical density was immediately measured with a spectrophotometer (Sunrise, TECAN, Männedorf, Zurich, Switzerland) at wavelengths of 540 and 600 nm. The cell viability percentage was evaluated in according to the manufacturer's protocol. The culture medium during experimental time was changed every two days.

Alkaline Phosphatase Assay

The alkaline phosphatase activity of the hMSC onto HA, GO, GO_SBF and HA-GO at different concentrations (1-1.5-2 wt %) was determined for 7, 14 and 21 days of culture by a spectrophotometric end-point assay that determined the conversion of colourless p-nitrophenyl phosphate as substrate to coloured p-nitrophenol following the manufacturer's protocol (Sensolyte pNPP ALP assay Kit, AnaSpec). Briefly, at the end of each time point, cultures were washed gently with PBS followed by washing twice with cold 1× assay buffer. For extract cell layers the cultures were lysing with 1× lysis buffer with 0.2% of Triton X-100. The phosphatase activity was analyzed onto the cell lysates (50 µl) by measuring the ALP activity when ALP enzyme catalyzes the cleavage of a phosphate group and release p-nitrophenol from p-nitrophenyl phosphate in alkaline buffer solution after 30 min at 37° C. Sample absorbance was measured in a 96-well plate at 405 nm. To correct the ALP values for the number of cells present on each scaffold double stranded DNA (dsDNA), was measured using a PicoGreen_dsDNA quantification kit (Invitrogen). First, 100 µl of 200 µl diluted Picogreen_dsDNA quantification reagent was added to 100 µl of cell lysates in a flat-bottomed, 96-well plate. Following 10 min incubation, the fluorescence of Picogreen was determined at a wavelength of 520 nm after excitation at 585 nm using a plate reader (multilabel counter 1420 Victor, Perkin-Elmer, Italy). dsDNA was quantified according to a calibration curve of 1-dsDNA standard in 10 mM Tris, 1 mM EDTA, pH 7.5, buffer. Each experiment was performed three times in triplicate. The results of ALP activity were reported as nanograms of ALP normalized to the micrograms of total DNA content.

Statistical Analysis

One-way analyses of variance (ANOVA) were performed to detect significant effects among treatment with post Bonferroni t-test. Results were considered to be significant at p<0.05.

RESULTS AND DISCUSSIONS

First Process: In situ Preparation of HA-GO
Thermogravimetric Analysis

Figure 2:
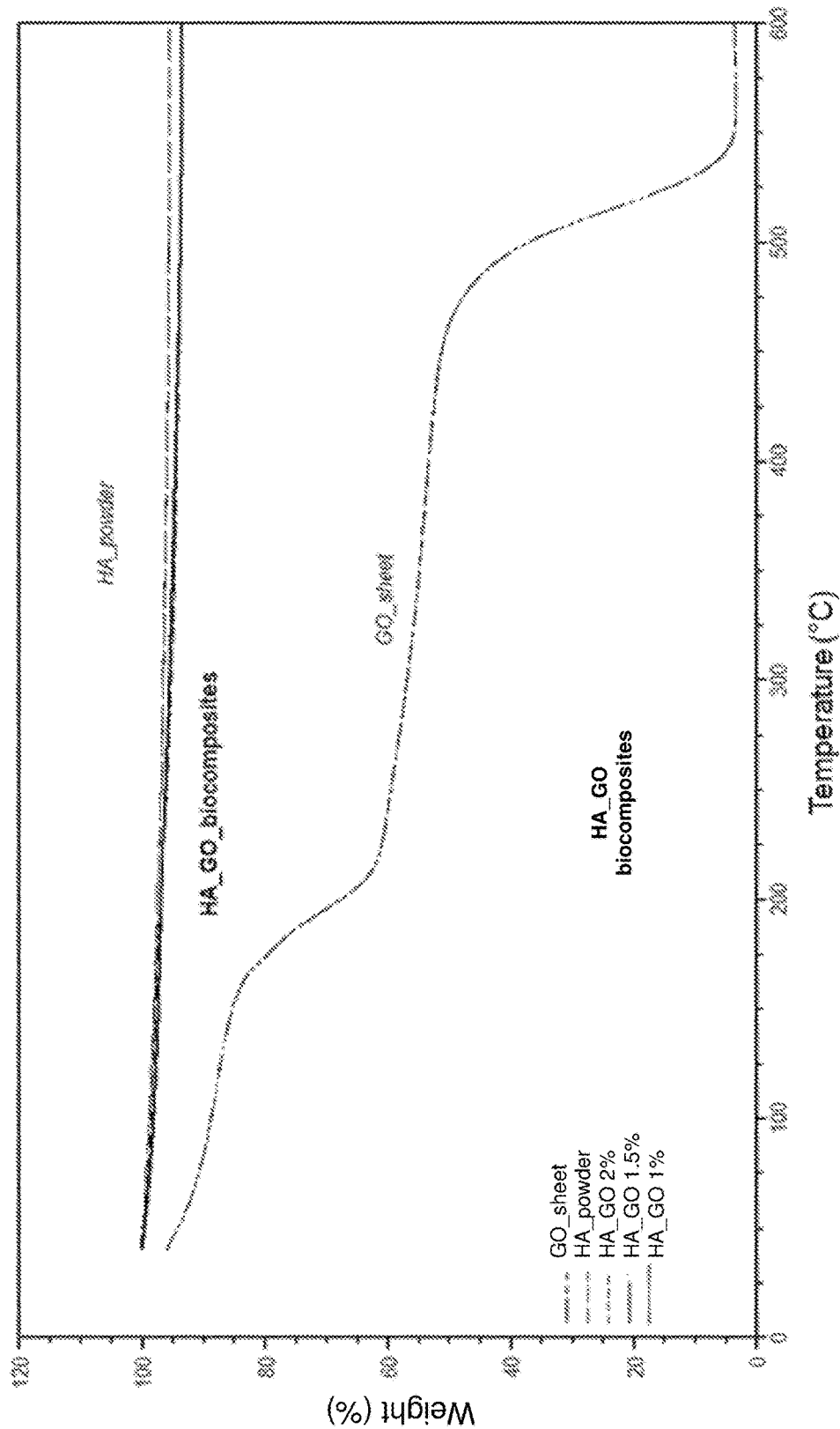
FIG. 2: TGA analysis of GO sheet, HA powders and HA-GO biocomposites at different composition (1-1.5-2 wt %)
Figure 2A:
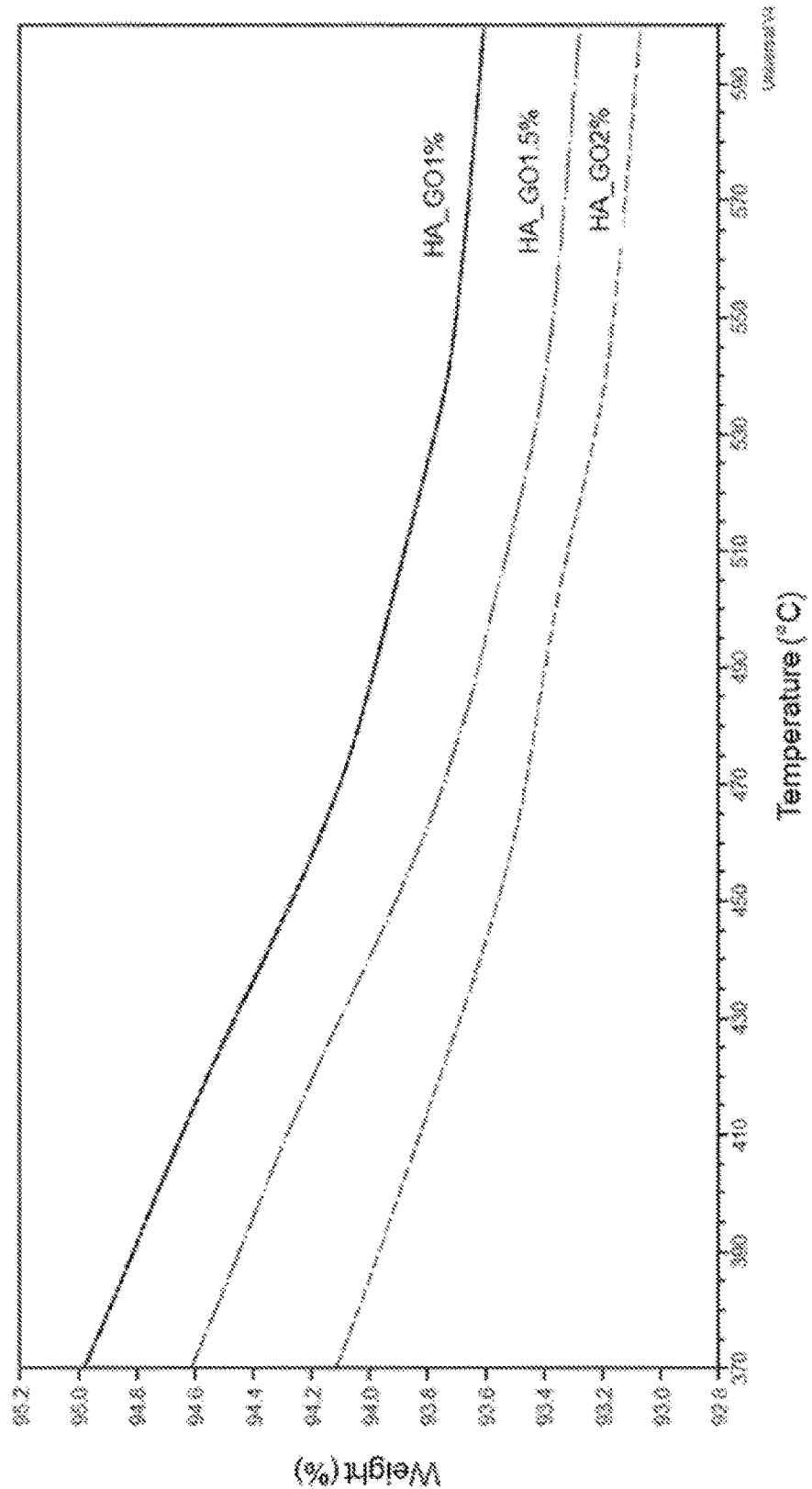
FIG. 2A is an enlarged view of the weight range 92.8-95.2%.

TGA analysis was conducted to test the thermal stability of GO sheet. Results were shown in FIG. 2. Three stages were observed in the quality loss cure of the GO sheet. Firstly, a roughly 8% quality loss occurred at the temperature of 100° C., primarily due to the loss of $H_2O$ molecules in the GO sheet layers. Secondly, the thermal decomposition of instable oxygen-containing functional groups showed a roughly 28% quality loss, occurring at a temperature of 195° C. Finally, a 55% quality loss occurred at 520° C. was mainly due to the combustion of the carbon skeleton.

The HA nanopowders and GO-HA nanocomposites suffered a very slow weight loss process from room temperature to 600° C. The TGA profile indicates an initial weight loss of all the samples around 100° C., that may be ascribed to the evaporation of absorbed water.

Furthermore, to analyze the GO content into the biocomposite, it was considered the thermal weight loss in the GO degradation range, between 370-570° C.; in this range, the curve lowering was dependent on the combustion of the carbon skeleton. The TGA analysis for HA-GO biocomposites at different compositions showed that the amount of GO in the materials is lower than the theoretical composition as reported in the Table 1. These results demonstrated that a part of GO introduced during the sol-gel reaction did not completely reacted with hydroxyapatite to form the final product.

TABLE 1

TGA analyses performed by Q5000

| SAMPLES | THEORETICAL COMPOSITION | | EVALUATED COMPOSITION by TGA | |
|---|---|---|---|---|
| HA-GO_1% | 99% HA | 1% GO | 99.07% HA | 0.93% GO |
| HA-GO_1.5% | 98.5% HA | 1.5% GO | 98.79% HA | 1.21% GO |
| HA-GO_2% | 98% HA | 2% GO | 98.25% HA | 1.60% GO |

X-Ray Diffraction and Infrared Spectroscopy FTIR Analyses

Figure 3A:
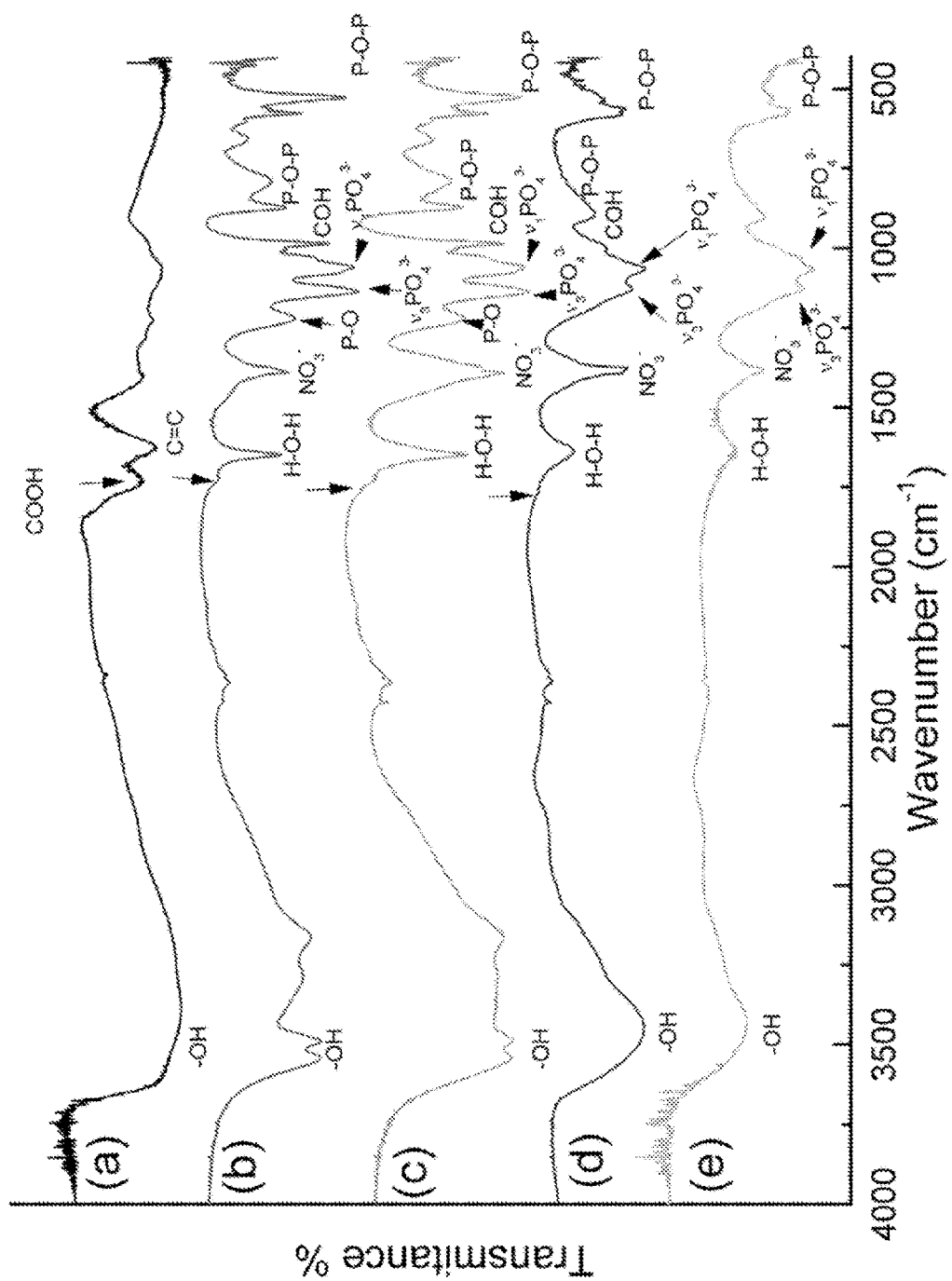
FIG. 3: (A) FTIR spectra of GO (a) HA-GO 1 wt % (b)—HA-GO 1.5 wt % (c)—HA-GO 2 wt % (d)—HA (e) and (B) XRD analyses of GO (a), HA (b)—HA-GO 1 wt % (c) HA-GO 2 wt % (d) prepared by sol-gel method.
Figure 3B:
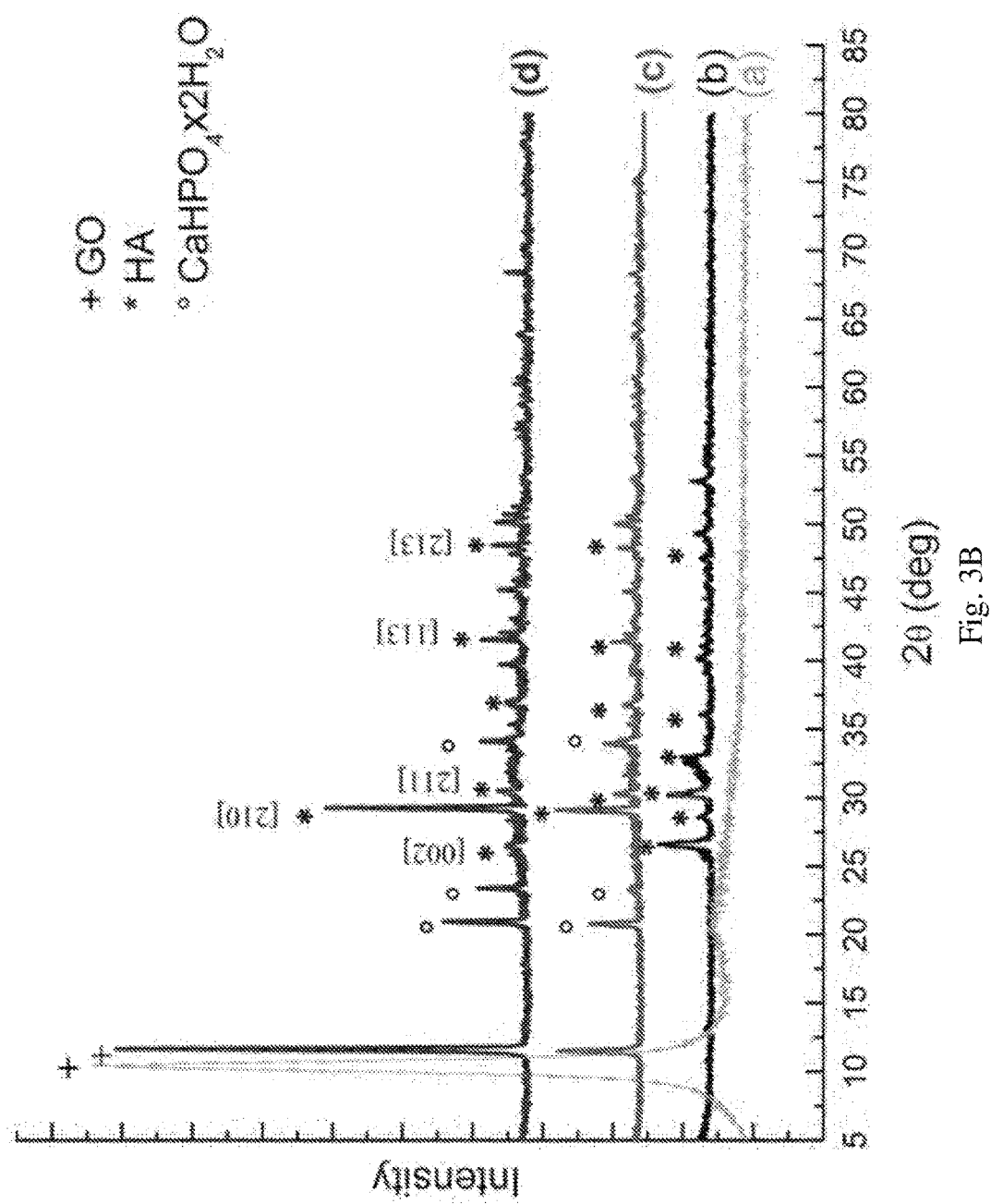

The oxygen-containing functional groups, such as hydroxyl and carboxyl identified by the FTIR analysis, present on the basal plane and edges of the GO sheets are important in anchoring calcium ions. The FTIR spectra of the GO, HA, and HA-GO at different compositions prepared in situ at room temperature are shown in FIG. 3A. The transmittance bands at 3400 $cm^{-1}$ were assigned to hydroxyl group (—OH) stretching, 1730 $cm^{-1}$ to the stretching vibration of carboxyl groups (—COOH) on the edges of the basal planes or conjugated carbonyl groups (—C═O), 1622 $cm^{-1}$ to the stretching vibration of aromatic C═C, 1266 $cm^{-1}$ to the stretching vibration of epoxide, 1054 $cm^{-1}$ to the stretching vibration of alkoxy RC—O—, and the 833 $cm^{-1}$ to the characteristic adsorption peak of epoxy groups. The presence of these oxygen-containing groups in GO spectrum reveals that the graphite has been completely oxidized. The polar groups, especially the hydroxyl groups, result in the formation of hydrogen bonds between graphite and water molecules; this explains the hydrophilic nature of GO. In the biocomposites HA-GO, the stretching band of phosphate at 1039 $cm^{-1}$ in pure HA shifted to 1037 $cm^{-1}$ and to 1033 $cm^{-1}$ in HA-GO, respectively, thus indicating the formation of strong hydrogen bonding between the HA nanoparticles and the GO-based sheets. Moreover, the band corresponding to epoxy group in GO (833 $cm^{-1}$) is shifted to 873 $cm^{-1}$ in the biocomposites, as well as the peak of COOH group (1730 $cm^{-1}$) decreases in intensity and it is shifted at lower wavenumber (1724 $cm^{-1}$), probably due to interaction between $COO^-$ groups and $Ca^{2+}$. The intense broad peak between 900 $cm^{-1}$ and 1100 $cm^{-1}$ is assigned to $PO_4^{3-}$. In the biocomposites, H—O—H bending gives rise to absorption at 1651 $cm^{-1}$, meanwhile the absorptions at 3545 $cm^{-1}$ and 3490 $cm^{-1}$ are due to intermolecular stretching and weakly H bonded OH because of water of crystallization. The peaks at 3284 $cm^{-1}$ and 3168 $cm^{-1}$ are assigned to $NH_4^+$ derived as a result of the byproduct of ammonium nitrate $NH_4NO_3$. In fact, during the synthesis, by increasing the amount of GO increases the acidic environment: for this reason more $NH_4OH$ was used to increase the pH value; an intense peak at 1384 $cm^{-1}$ is related to $NO_3^-$ ions. The absorption at 1217 $cm^{-1}$ is due to P—O associated to aromatic ring of GO. The P—O—P asymmetric stretching vibrations give rise to absorptions at 985 $cm^{-1}$ and 784 $cm^{-1}$. In the FTIR spectra of HA-GO 1.5 (c) and 2 wt % (d), it is possible to evaluate also the presence of typical peaks of calcium hydrogen phosphate dehydrate at 665 $cm^{-1}$ due to (H—O—)P═O, as also confirmed in XRD spectra (FIG. 3B). However, the stretching and the bending modes of $PO_4^{3-}$ appeared at 602 $cm^{-1}$ and 562 $cm^{-1}$ as intense sharp peaks. Moreover, the evaluation of the phases of the GO, HA, and HA-GO (1 and 1.5wt %) were investigated by XRD (FIG. 3B). The Bragg diffraction peaks of the two GO-based HA composites, shown in FIG. 4A, agreed quite well with those of the pure synthesized HA (PDF# 09-0432) at 2θ values of 25.9°, 28.9°, 31.8°, 39.8°, 46.7°, 49.5° and 53.2°, which were indexed to be (002), (210), (211), (310), (222), (213) and (004) planes, respectively. Meanwhile, the peaks at 21.2°, 23.2° and 34.5° match (PDF# 03-0836) with calcium hydrogen phosphate dihydrate ($CaHPO_4 \times 2H_2O$) precursor of hydroxyapatite. This data is in agreement with the FTIR peaks of $NH_4^+$ and $NO_3^-$ reported above (FIG. 3A). Meanwhile, the broad diffraction peaks suggested that the prepared HA particles were nanocrystallites, which were proposed to have superior osteointegrative properties toward micro HA, and were much easier to be embedded or incorporated into the GO matrix. The strong and sharp (002) peak of the GO sheets at 2θ=10° corresponds to d-spacing of 0.9 nm; it was shifted and became more sharp in the composites, probably due to the loss of their crystallographic order after being treated by ultrasonic dispersion and the intercalation of the HA nanoparticles (FIG. 3B).

Morphological Characterization

Figure 4:
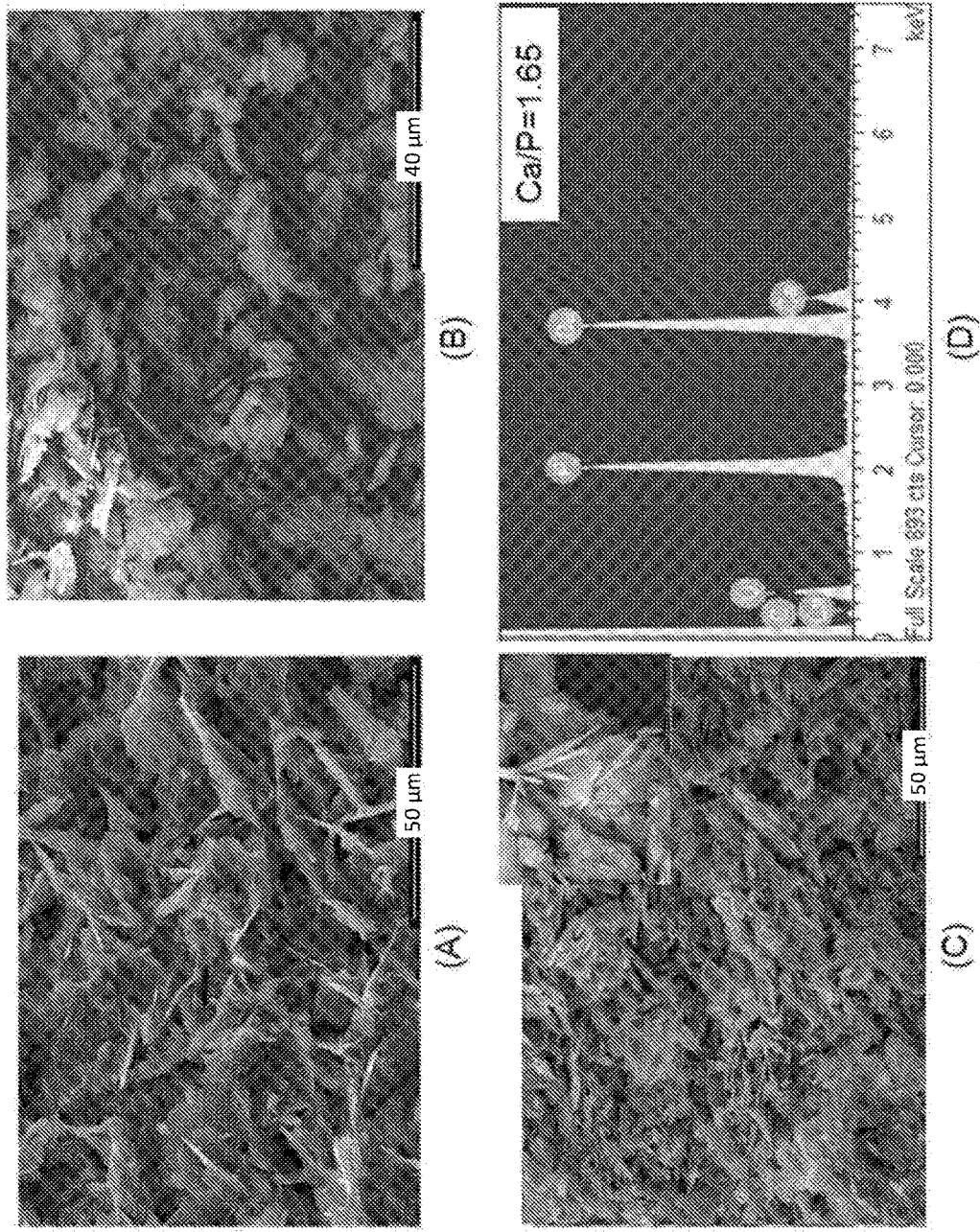
FIG. 4: SEM images of HA-GO 1 (A)—1.5 (B)—2 (C) wt %; EDS analysis performed on HA-GO 2 wt % (D)

SEM images performed on HA-GO biocomposite materials demonstrated a good intercalation of HA nanoparticles in GO sheet and any clusters were observed for materials obtained at 1-1.5 and 2 wt % of GO (FIG. 4A-C). The Ca/P ratios of HA formed in graphene oxide determined by EDAX analysis (FIG. 4D) were about 1.65, slightly lower than the stoichiometric ratio of Ca/P in HA (1.67), but close to that of natural bone, which were thought to endow the biocomposites with higher bioactivity.

Figure 5:
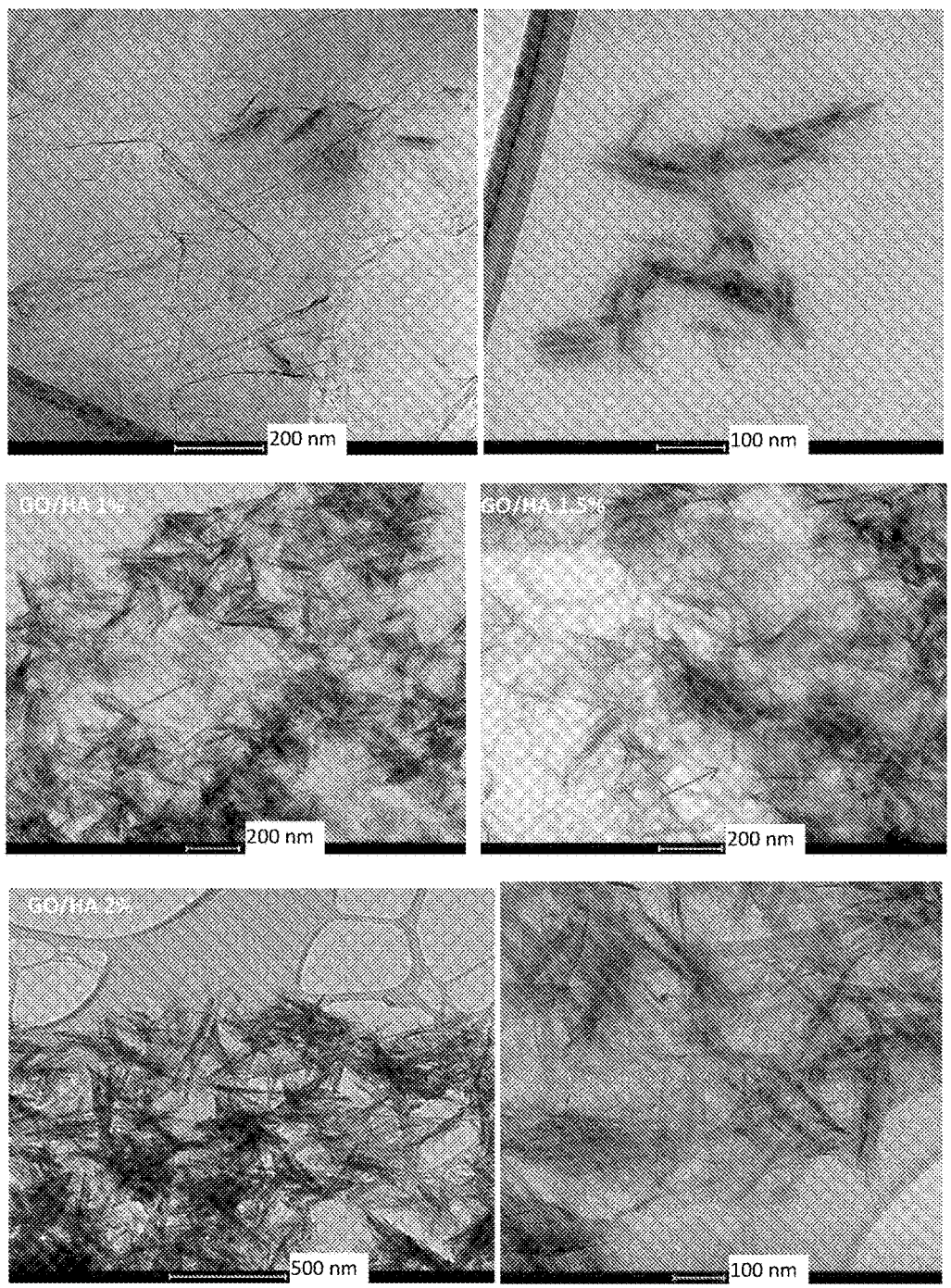
FIG. 5: TEM analysis of GO, HA and HA-GO at different concentrations.

More information are obtained by TEM analysis. The TEM images of GO sheet (FIG. 5A) demonstrated a good exfoliation of material after ultrasonic treatment and it is possible to evaluate that the presence of sheet modeling the distribution of ceramic nanoparticles. In fact, increasing GO amount a better dispersion is observed. This behavior could be explained because the sol-gel reaction allows a good interaction between the oxygenated regions in hydrophilic zones, of GO and HA nanoparticles. Moreover, the uniformly dispersion is explained by nanometric size of hydroxyapatite synthesized by sol-gel method as demonstrated by TEM analysis (FIG. 5). The HA particles were in a typical spindle-like shape with a diameter of about 5±0.37 nm and a length of around 70±2.5 nm on the GO sheets. In the present study, the HA-GO samples were treated ultrasonically before TEM observation, it can be seen that almost no HA particles are scattered out of the matrix, indicating a strong interaction between the HA particles and the GO. The high specific surface area of GO is also beneficial for high loading levels of the HA particles and is helpful for forming an effective network inside the biocomposite. It was reported that GO behaved like an amphiphilic macromolecule with hydrophobic zones (the graphenic $sp^2$ hybridized carbon plane) randomly embedded in hydrophilic zones (the oxygenated regions and the sheet edges). Furthermore, as verified from the TEM observations these nanoparticles were randomly decorated on the GO surface as well as the sheet edges. Besides, the carbonyl groups on the periphery of the basal planes had higher chemical affinity toward $Ca^{2+}$ cations than the basal planes, and Ca atoms were favorably adsorbed on the edges, which could result in the grafting and aggregation of HA nanoparticles on the GO sheet edges.

Bioactivity Test

Figure 6:
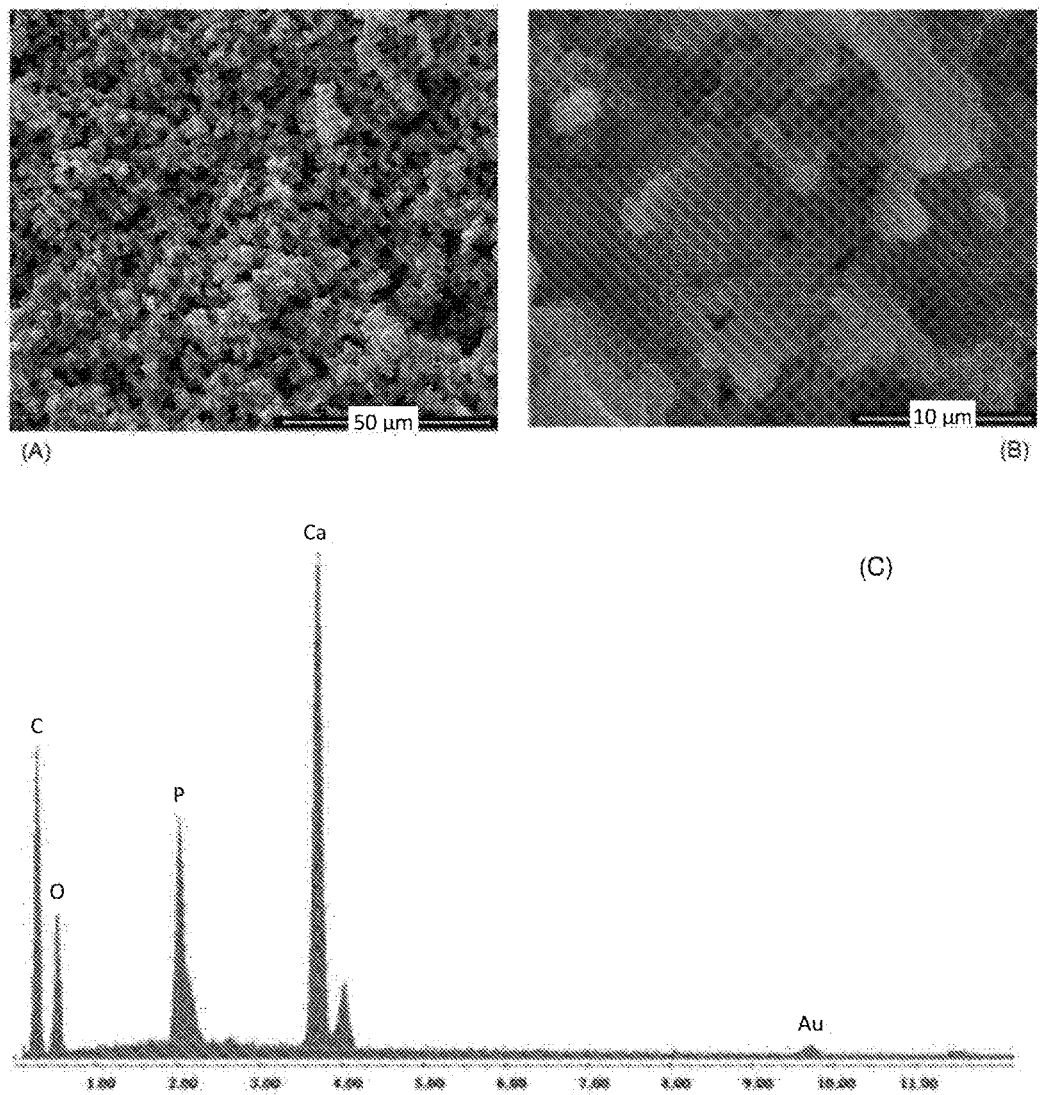
FIG. 6: SEM images of HA-GO 1.5 wt % after SBF treatment on surface (A) and in cross-section (B). EDS analysis after 5 days of SBF treatment (C)

SEM observations performed on HA-GO 1.5 wt %, incubated for a shorter time (7 days) in a SBF solution further revealed that graphene-hydroxyapatite hybrid material shows a good bioactivity with the deposition of HA crystals (FIG. 6) on the surface and in cross-section of HA-GO, demonstrating that a hybridization of HA nanoparticles in GO sheet increases the bioactive properties of materials after SBF treatment. This is confirmed by the presence of coating on surface and some depositions of calcium phosphate intercalated among the GO sheets (FIGS. 6A-B).

The analyses show that the rose petal-like apatite crystallites are composed mainly of hydroxyapatite, with a Ca/P molar ratio of about 1.65. The EDAX spectra clearly shows Ca and P peaks, which are typical of hydroxyapatite (FIG. 6C), and smaller peaks of sodium, chlorine and magnesium due to the presence of impurities commonly present in biomimetic apatite.

Second Process: Biomimetic Method to Prepare Biomineralized GO Sheets

X-Ray Diffraction and Infrared Spectroscopy FTIR Analyses

Figure 7A:
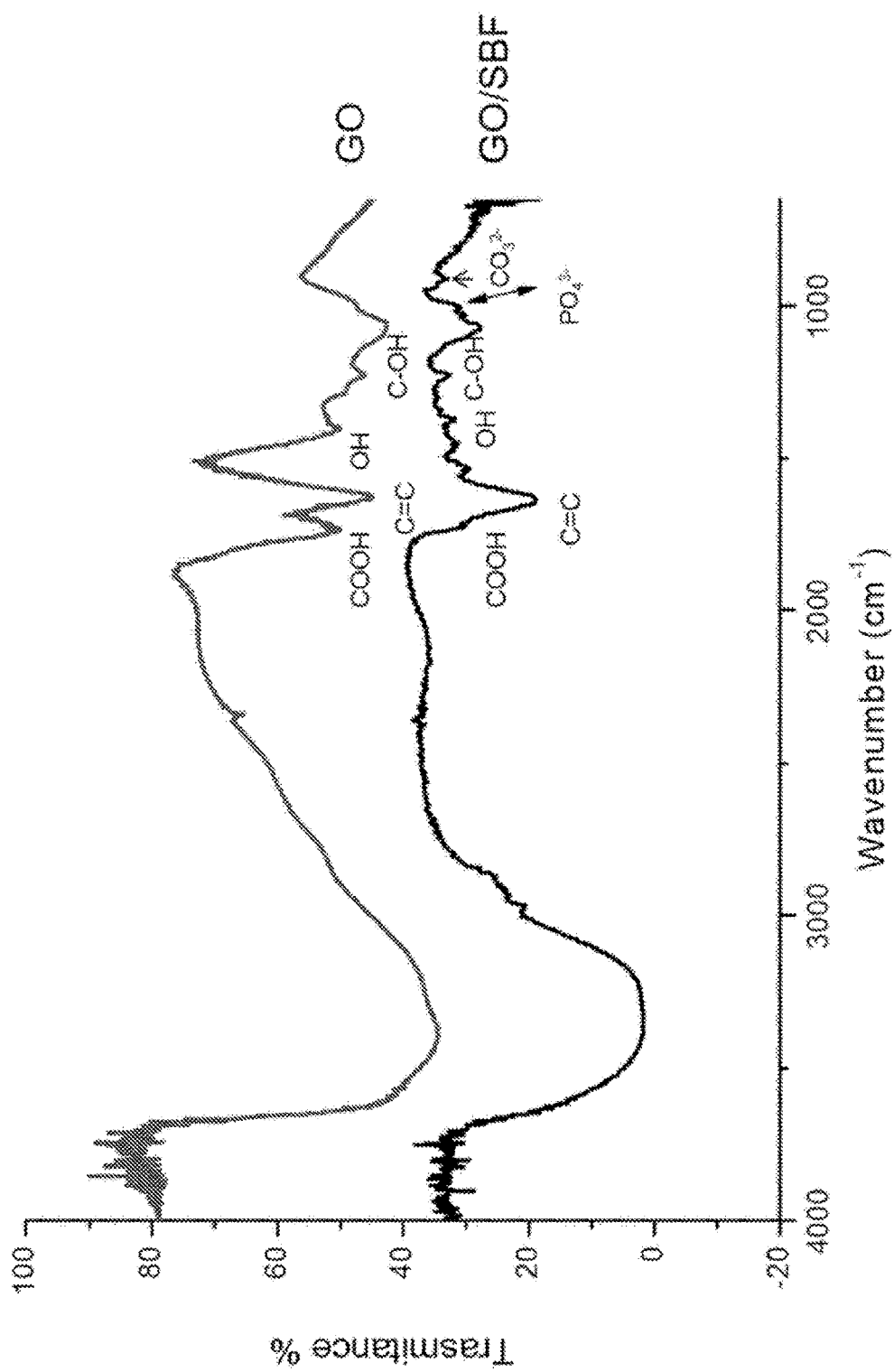
FIG. 7: FTIR (A) and XRD (B) analyses of biomineralized GO prepared by biomimetic approach.

The FTIR spectra of the GO sheet before and after SBF treatment are shown in FIG. 7A. The spectrum of GO after biomimetic treatment allows for the evaluation of presence of COOH peak at 1730 $cm^{-1}$ and the stretching vibration of epoxy C—OH at 1266 $cm^{-1}$, 1054 $cm^{-1}$ to the stretching vibration of alkoxy C—O, meanwhile it was possible to observe the stretching band of phosphate at about 1100 $cm^{-1}$ that was assigned to $PO_4^{3-}$. The stretching and bending modes of $PO_4^{3-}$ appeared approximately at 562 $cm^{-1}$, meanwhile the peak appeared at 920 $cm^{-1}$ suggesting the presence of carbonate ions $CO_3^{2-}$.

Figure 7B:
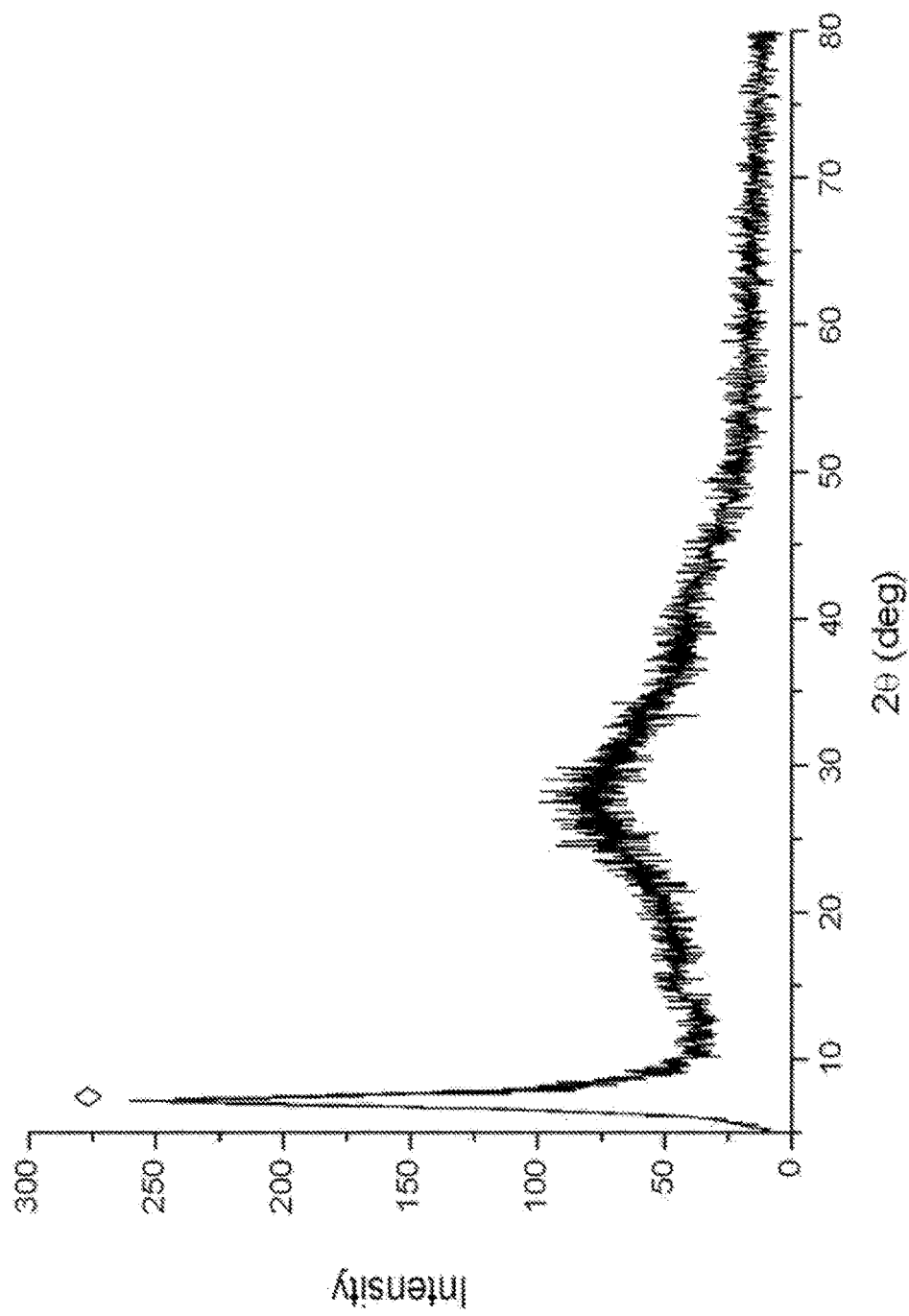

Furthermore, the phases of the GO_SBF was investigated by XRD and it demonstrated that an amorphous state appears in biomineralized composite obtained by biomimetic approach (FIG. 7B). This result could be explained by the presence of chemical groups on GO sheet which promote the nucleation of calcium phosphate on the surface, meanwhile a short treatment involving only 2 days of incubation (5×$SBF_2$) for growth and crystallization delay the crystallization of hydroxyapatite.

Morphological Characterization

Figure 8:
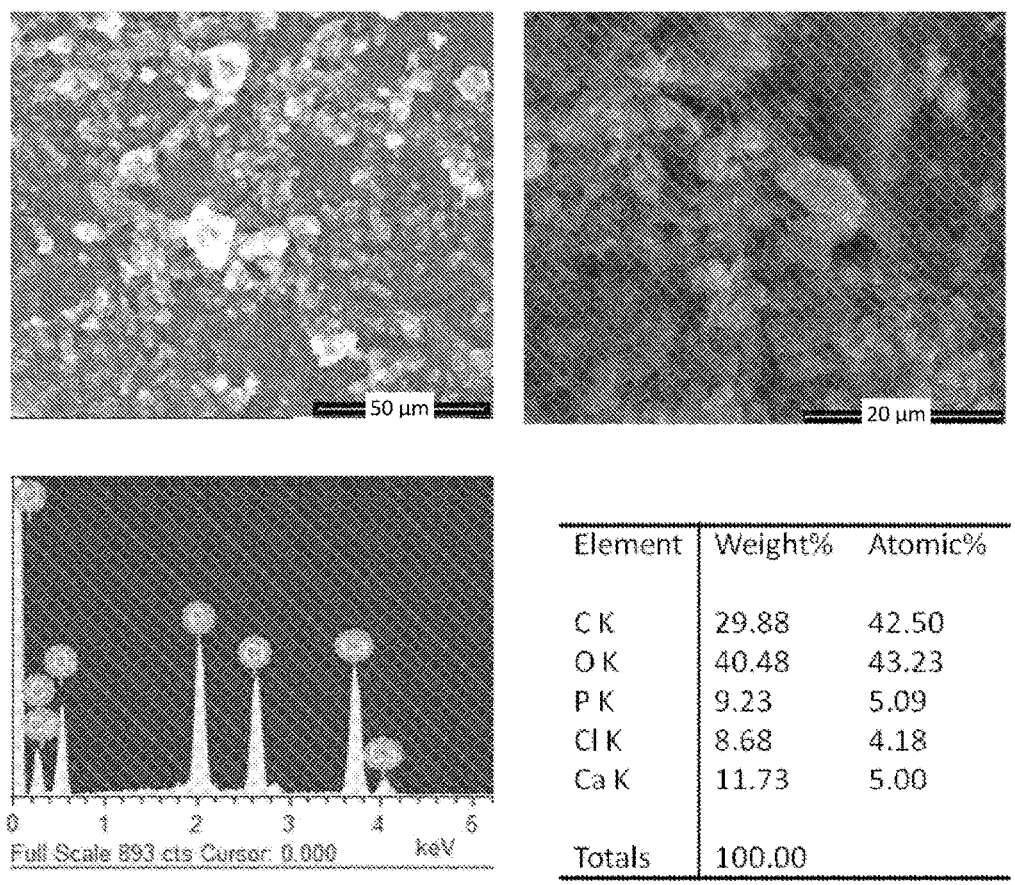
FIG. 8: SEM images and EDS analysis of GO sheet after 7 days SBF treatment.

The biocomposite material prepared by biomimetic approach (first process) shows a different morphology than biocomposites prepared by sol-gel approach (second process). In fact, SEM/Energy Dispersive X-ray Spectroscopy (EDAX) image of GO sheets after treatment in supersaturated 5×SBF solutions is shown in FIG. 8. The image shows that after 3 days of soaking in 5×$SBF_1$, followed by immersion for 2 days in 5×$SBF_2$, the GO sheet was covered by a calcium phosphate layer (FIG. 8A-B) and the EDAX analysis demonstrates that the Ca/P molar ratio is about 1.0 that could correspond to the amorphous calcium phosphate (FIG. 8C).

Figure 9:
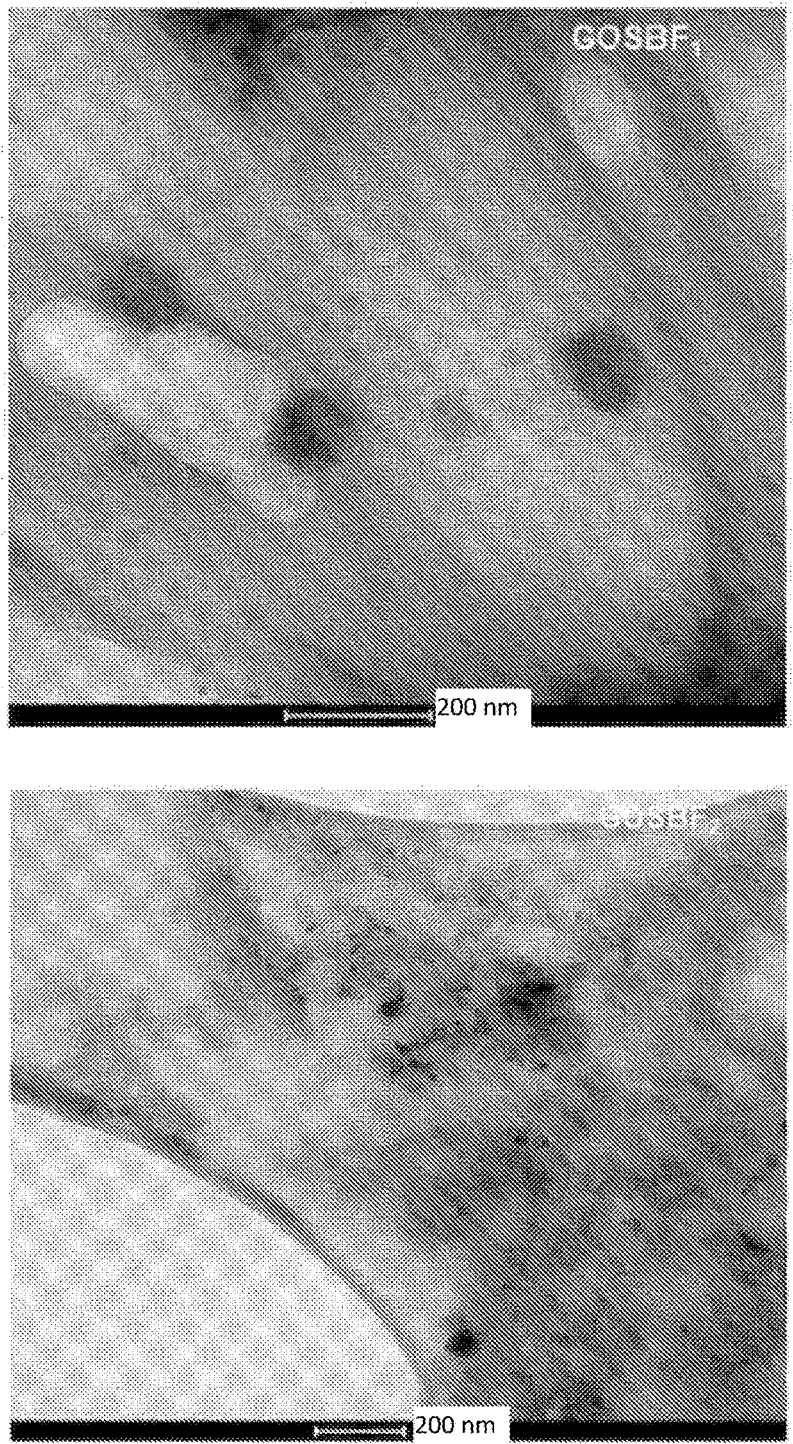
FIG. 9: TEM analysis of GO sheet after 5×$SBF_1$ and 5×$SBF_2$ treatments, respectively.

Furthermore, TEM analysis (FIG. 9) clearly showed that the particles of calcium-phosphate were nanosphere-like and not nanocrystalline HA with acicular shape as shown for nanocomposite HA-GO and in accordance with SEM results (FIG. 8).

Biological Results

There is no doubt that the material used for bone tissue engineering should be non-toxic and have good cell biocompatibility, which is a central criterion that ultimately decide the feasibility of implantation in body. The information of proliferation on the materials provided by cell culture experiment in vitro is often used as an important initial evaluation of cell biocompatibility. Human mesenchymal stem cells (hMSC), largely used to evaluate the regeneration of mineralized ECM in bone defects, were used as a cell line model for in vitro testing of biocompatibility and osteogenic potential of the HA-GO materials.

Figure 10:
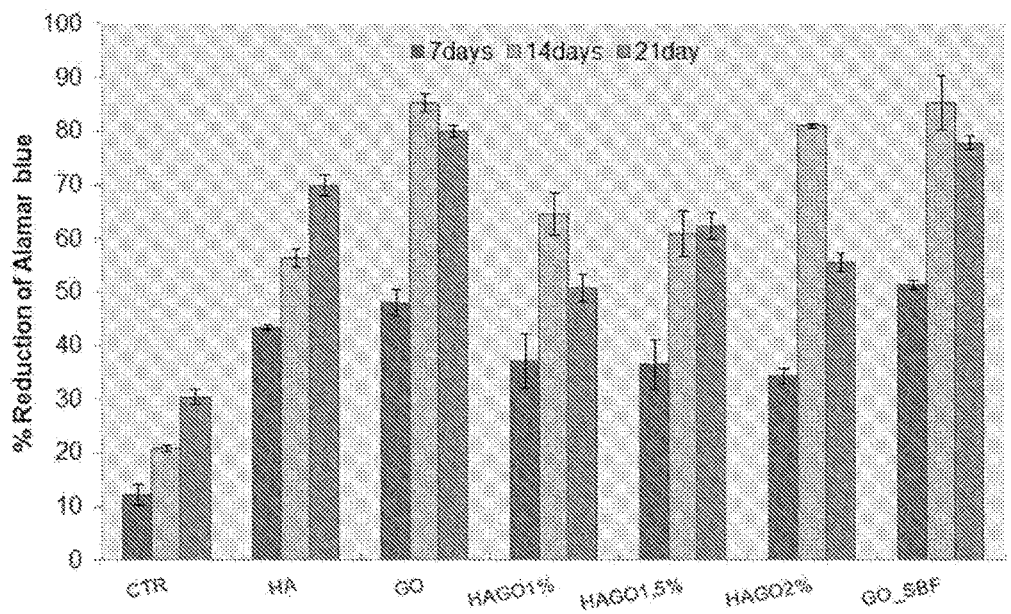
FIG. 10: Alamar blue of GO, HA, HA-GO (1-1.5-2 wt %) and GO_SBF at 7, 14 and 21 days.

The cell proliferation on the different materials (HA, GO, HA-GO, GO_SBF) were assessed by using Alamar Blue test. FIG. 10 shows the effect of the materials on the metabolic activity of hMSC after 7, 14 and 21 days of culture. According to the data, it can be found that the number of hMSCs dramatically increase with time during the in vitro culture period; suggesting that the materials are nontoxic, not affecting the cell proliferation and showed good biocompatibility. In particular, the results showed that the cell proliferation is better for GO sheets than HA material, this is explained by the presence of active group and a charge surface. Moreover, GO_SBF materials after SBF treatment show a good proliferation within a similar time frame when compared to GO sheets. This result could be explained by a large surface of GO in contact with cells and the presence of small clusters of amorphous calcium phosphate have a negligible effect on cell proliferation. Meanwhile, in the composite materials a slight decreasing of proliferation activity was observed though higher value than the control samples.

Besides the amount of the proliferated cells, the differentiation of the cells should be another important parameter to estimate the biological effect of calcium phosphate particles. ALP activity assay (FIG. 11) was used to evaluate the differentiation of hMSCs on the different composite materials (HA, GO, HA-GO, GO_SBF).

The present studies of the differentiation of hMSCs towards the osteoblastic-like phenotype was quantitatively determined by carrying out a destructive assay for ALP activity using the p-nitrophenyl phosphate method. ALP is an enzyme produced by differentiating osteoblasts and is present both on the extracellular membrane and in vesicles of the bone matrix, which is the initial site of the formation of calcium phosphate crystals. The enzymatic activity of ALP is crucial for the mineralization process; it acts on the organic phosphate to increase the local concentration of free phosphate and to induce the active transport of both phosphate and calcium across the cell membrane. ALP is an important feature of osteoblast cells expressed in their differentiation phase and a significant quantitative marker of osteogenesis.

Figure 11:
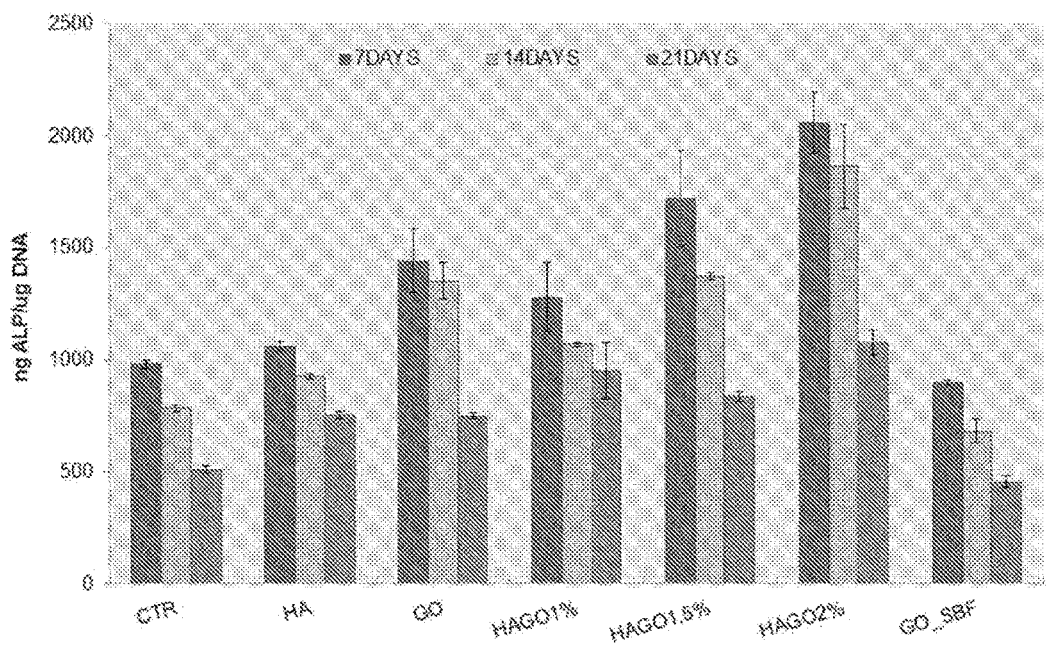
FIG. 11: ALP assay of GO, HA, HA-GO (1-1.5-2 wt %) and GO_SBF at 7, 14 and 21 days in basal medium.

The in vitro ALP activity of hMSC cells cultivating with HA-GO hybrids was evaluated. As shown in FIG. 10, the combination of HA and GO allowed the ALP expression in the first days of cell-materials interaction to be observed early. The FIG. 11 showed that for GO and biocomposite obtained by sol-gel approach the ALP value are highest in the first 14 days; in particular it is possible to observe the increasing ALP value with the increasing amount of GO in composite materials. Meanwhile the ALP values for GO sheet after SBF treatment were similar to control (CTR) and lower than the biocomposite materials. This result might be due to amorphous state of calcium phosphate clusters deposited on GO surface that delay the expression of ALP from hMSC in a basal medium without osteogenic factors like ascorbic acid, dexamethasone and β-glycerophosphate.

Example 4

Figure 12:
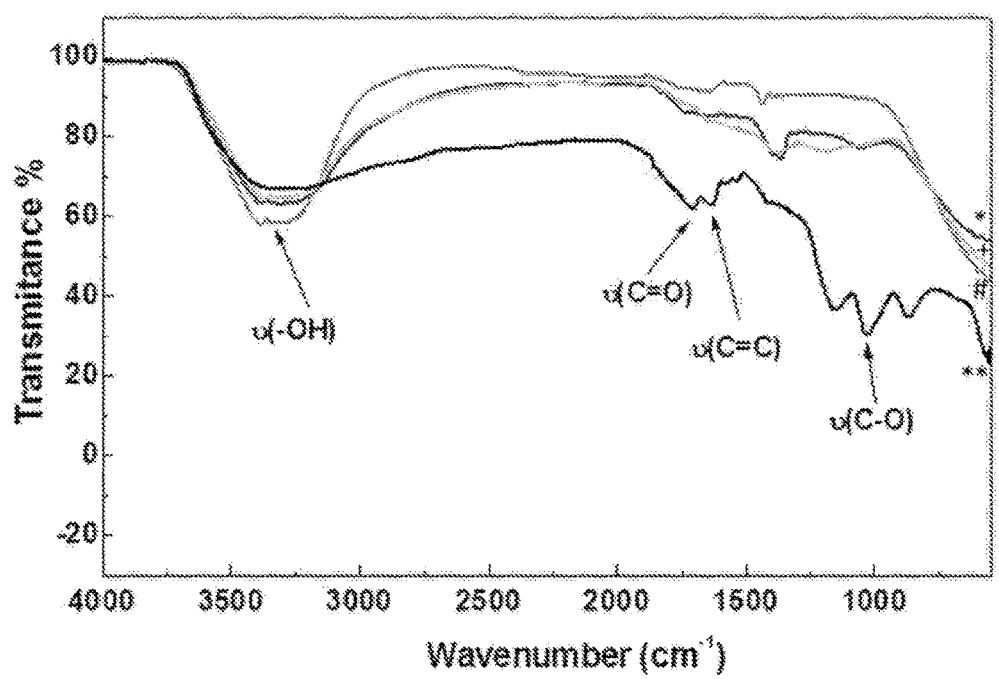
FIG. 12: ATR spectra of GO, HA-GO 1-1.5 and 2 wt % after HCl treatment (1M), as per Example 4.
Figure 13:
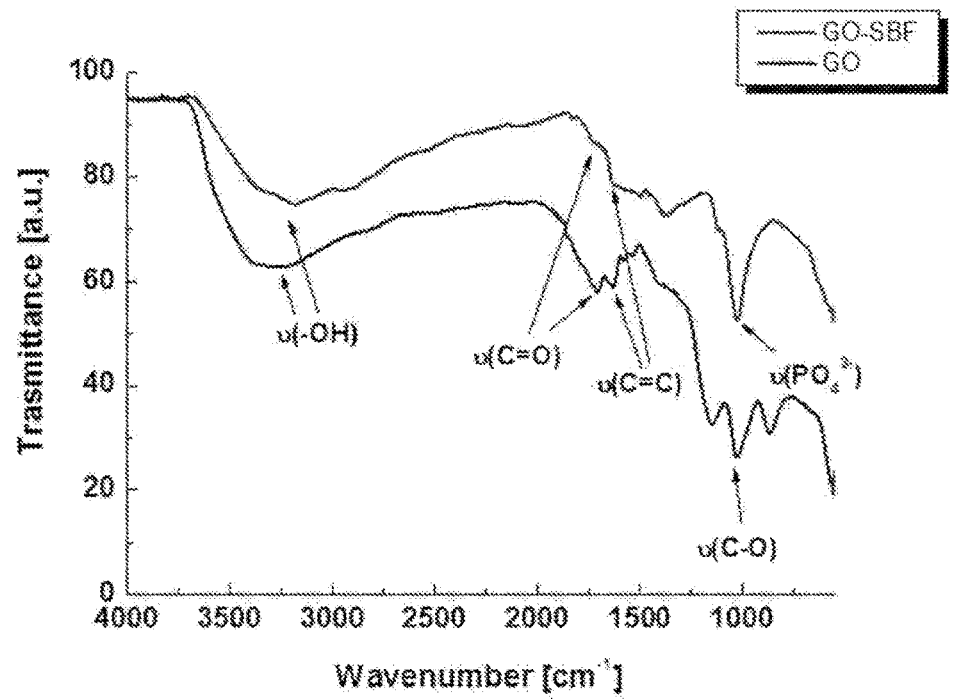
FIG. 13: ATR spectra of GO paper and GO paper after SBF treatment, as per Example 4.

Test of Aging the Biocomposite of the Invention
Materials and Methods
Material Production: First Process (Sol-gel Approach)
Biomineralized materials (HA-GO 0.5-1.0-1.5-2.0 wt %) obtained by the first process of the invention underwent an aging of 3 days at 60° C. In order to remove the calcium phosphate component and to evaluate the effective reduction of residual graphene oxide to graphene, a sample treatment with HCl (1M) was performed, while working at room temperature for 10 min in an ultrasound bath. Then, ATR and fluorescence investigations were performed. Furthermore, the effect of materials on induction of oxidative stress of human primary osteoblasts (HOBs) was also performed.
Material Production: SBF Treatment
The second process of the invention (SBF treatment) was performed on the GO film at room temperature for a period of 7 days in 5×SBF$_1$ and 5 days in 5×SBF$_2$ changing the solutions every 2 days.
The second process further comprises an aging of the biocomposite of at least one day at a temperature of at least 50° C., preferably for about two days at a temperature of about 60° C.
Attenuated Total Reflectance Analysis (ATR)
ATR spectroscopy was performed on Perkin Elmer Frontier system 550-4000 cm$^{-1}$ region (4 cm$^{-1}$ resolution, average 64 scans).
Luminescence Analysis
The materials re-suspended in distilled water were investigated by luminescence analysis. The emission and excitation spectra were obtained using a Perkin Elmer LS55 system.
Biological Investigation
Intracellular Reactive Oxygen Species (ROS) Measurement
The generation of intracellular reactive oxygen species (ROS) was evaluated by using the fluorescence probe 2',7'-dichlorfluorescein-diacetate (H2DCF-DA). For the experiments, osteoblasts were plated in 96-multiwell black plates at the density of 1×104 cells/well. Cells were cultured for 24 h at 37° C. in presence and in absence of scaffolds (HA, HA-GO 0.5-1.0-1.5-2.0wt %, GO paper and GO_SBF). After washing, cells were incubated for 1 h with 200 μl of 100 μM H$_2$DCF-DA in HBSS containing 1% FBS. Finally, cells were rinsed and incubated with the Fenton's reagent (H$_2$O$_2$/Fe$^{2+}$ 2 mM) for 3 h at 37° C. The DCF fluorescence intensity was detected by using a fluorescent microplate reader (excitation 485 nm and emission 538 nm). The intracellular ROS levels were expressed as fluorescence intensity (picogreen).
Results and Discussion
Attenuated Total Reflectance Analysis (ATR)
The ATR of HA-GO after dissolution treatment by HCl (1M) are reported in FIG. 12. The results demonstrated that after dissolution treatment by HCl, numbers of absorption bands and their intensities in the extracted graphene decreased from 1 wt % to 2 wt % of HA-GO in comparison with original Graphene oxide.
Indeed, the C=O stretching mode completely disappeared, and the C=C stretching peak was slightly shifted from 1630 cm$^{-1}$ to 1582 cm$^{-1}$, probably as a consequence of the conjugation extension in the graphene sheet.
The ATR spectra of the pure GO paper before and after SBF treatment are shown in FIG. 13. The spectrum of GO sample after 12 days of 5×SBF treatment allows to evaluate the stretching band of phosphate at about 1100 cm$^{-1}$ that was assigned to PO$_4^{3-}$, meanwhile it is possible to observe a drastic reduction with a slight shift of COOH and C=C peaks at 1721 cm$^{-1}$ and 1632 cm$^{-1}$, respectively:

| | cm$^{-1}$ | GO | cm$^{-1}$ | GO-SBF |
|---|---|---|---|---|
| O—H | 3351 | broad, strong | 3297 | broad, weak |
| C—H | 2779 | weak | 2901 | weak |
| C=O | 1712 | strong | 1721 | weak |
| C=C | 1614 | strong | 1632 | strong |
| C—O | 1030 | strong | — | — |
| PO$_4^{3-}$ | — | — | 1022 | strong |

Figure 14:
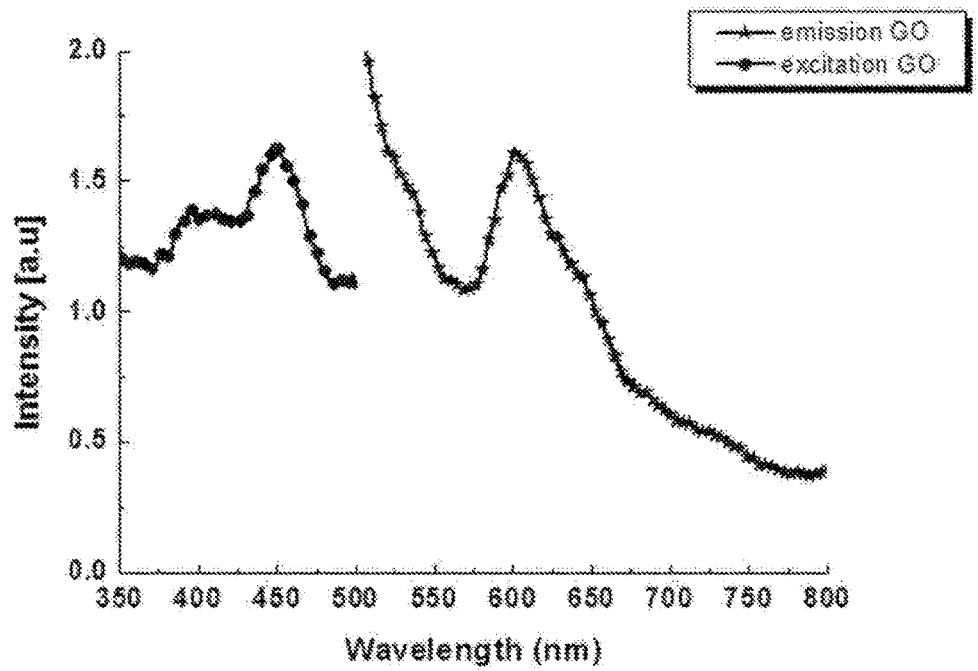
FIG. 14: Emission and excitation spectra of graphene oxide, as per Example 4.
Figure 15:
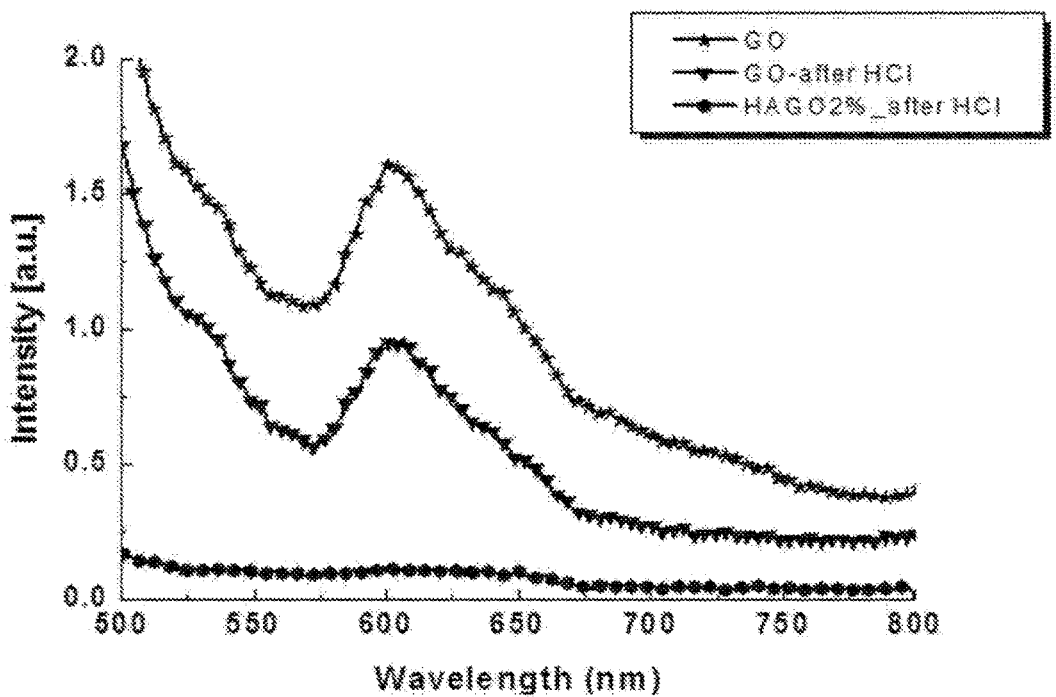
FIG. 15: Emission spectra of neat Graphene oxide (GO); GO treated with HCl 1M and HA-GO 2 wt % after HCl treatment, as per Example 4.
Figure 16:
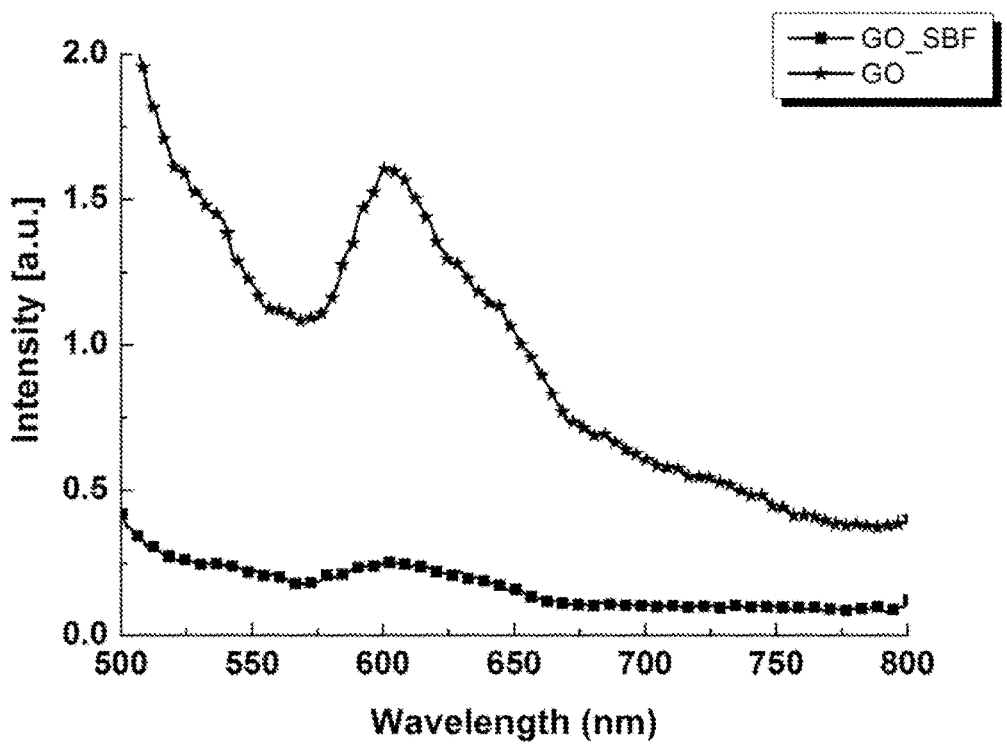
FIG. 16: Emission spectra of Graphene oxide paper before and after SBF treatment (12 days), as per Example 4.
Figure 17:
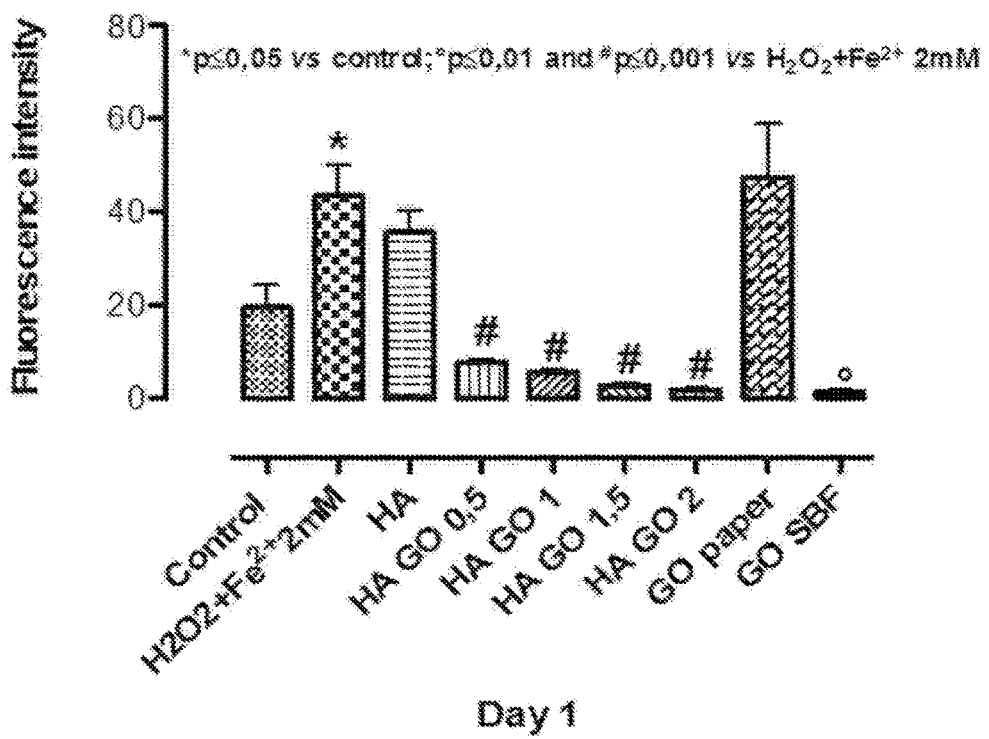
FIG. 17: ROS production after 24 hrs of cell incubation, as per Example 4.

Fluorescence Analysis
In order to confirm the ATR results concerning the full GO conversion to graphene, GO fluorescence signal was accurately investigated by Photoluminescence spectroscopy. FIG. 14 shows the excitation and emission spectra of GO suspension in distilled water. The sample has an excitation band at ca. 450 nm, which leads to a photoluminescence (PL) signal with maximum at ca. 609 nm. As well-known, GO can emit radiation in the near-infrared, visible and ultraviolet regions, however the mechanisms, responsible for PL in GO, are not yet completely explained. Probably, the fluorescence signal is generated in the GO molecules by the presence of small area of conjugated carbon-carbon double bonds. In the FIG. 15, it was compared the emission spectra of GO, GO after dissolution treatment by HCl and the extracted graphene obtained from HA-GO 2%. The results showed a complete disappearance of fluorescence for extracted graphene; the emission spectra of pure GO after HCl dissolution treatment confirms its complete inertness to HCl. Meanwhile, a disappearance of fluorescence was obtained for graphene oxide after SBF treatment for 12 days, as shown in FIG. 16.
Intracellular Reactive Oxygen Species (ROS) Measurement
Inflammation involves a multitude of processes. It entails the production of an amount of energy sufficient to support all necessary biochemical reactions and the output of all mediators, such as proteins. The energy is provided by ATP, which is produced in the mitochondria via the electron-transport chain and oxidative phosphorylation. This implies an oxidation process with oxygen as the main combustive agent. The biochemical reaction involved in oxidation of molecules, with the aim of producing energy, gives rise to reactive oxygen species (ROS). The most important free radicals in biological systems are radical derivatives of oxygen. All are very reactive and can oxidize a range of different biological molecules. To remain healthy, organisms need to maintain equilibrium between the production of free radicals in the energy process and the damaging effects, known as oxidative stress. The well-being of organisms depends on the activity of efficient defense systems against the oxidative damage induced by ROS. Mitochondria are the main intracellular source, and the immediate target, of ROS. Defects in the respiratory chain, in the affected tissues of patients with mitochondrial disease or in aged individuals, may contribute to an increased production of superoxide anions by mitochondria, that are very susceptible to oxidative damage generated in situ. It can be assumed that changes in the oxidation processes of mitochondria can affect the inflammatory process. On this basis, the materials were incubated with osteoblast cells (24 hrs) and their effect on the ROS production was evaluated. As shown in FIG. 17, the exposure of osteoblasts to $H_2O_2/Fe^{2+}$ (2 mM) produced a significant increase (*$p \leq 0.05$) in ROS formation, a pretreatment with HA-GO 0.5-1-1.5-2 wt % for 24 h significantly ($p \leq 0.01$ and #$p \leq 0.001$) reduced ROS production as measured by the inhibition of DCF fluorescence intensity. By contrast HA and GO paper did not prevent ROS production. The results in combination with biological investigations as herein reported demonstrate a full biocompatibility of biomineralized graphene materials.

It is demonstrated the possibility to produce biomineralized hydroxyapatite nanoparticles/graphene oxide by two different and simples approaches using non toxic components. In the first approach based on in situ synthesis by sol-gel method, spindle-like HA nanoparticles (diameter: 5 nm; length: 70 nm) were obtained, intercalated uniformly and strongly with the GO sheets. The interaction between HA nanoparticles and GO improved the bioactivity of materials demonstrated by the formation of a hydroxyapatite layer on material surface after biomimetic treatment. Moreover, the formed HA-GO hybrids supported high viability of hMSC cells and induced an osteogenic differentiation evaluated by using a media without osteogenic factors. The second approach was represented by using a simple biomimetic method based on supersaturated 5×SBF solution. A layer of amorphous calcium phosphate (ACP) appeared on GO sheet after 5 days of incubation. The composite sustained the cell viability and proliferation, however it delayed the expression of ALP, early marker of osteogenic differentiation, in a basal medium. In vitro bioactivity and biocompatibility of biomineralized graphene materials present the new prospect to develop a broad new class of multi-functional biomaterials for clinical and biomedical applications.

The invention claimed is:

1. A process for preparing a biocomposite of hydroxyapatite and calcium phosphate on graphene oxide sheets, the process comprising the steps of:
   i) providing and sonicating an aqueous solution of graphene oxide to exfoliate graphene oxide sheets,
   ii) providing an aqueous solution of a Calcium salt selected from nitrate, sulphate, hydrogen sulphate, carbonate, chloride, nitride, and combinations thereof,
   iii) adding the aqueous solution of step ii) to the aqueous solution of step i),
   iv) providing an aqueous solution of a phosphorus salt selected from dihydrogen phosphate, hydrogen phosphate, phosphate, dihydrogen phosphite, hydrogen phosphite, phosphite, and combinations thereof, and
   v) adding the aqueous solution of step iv) to aqueous solution obtained in step iii), and gelating by adjusting to alkaline pH, thus obtaining the biocomposite.

2. The process of claim 1, wherein, in the aqueous solution obtained in step v), the molar ratio between calcium and phosphorus is 1.0 to 3.0.

3. The process of claim 1, further comprising a step vi) of aging the biocomposite obtained in step v) for at least one day at a temperature of at least 50° C.

4. The process of claim 1, wherein, in step i), the aqueous solution of graphene oxide is sonicated at room temperature for at least 2 hours.

5. The process of claim 1, wherein aqueous solution obtained in step iii) is ultrasonicated at room temperature for at least 20 minutes.

6. The process of claim 1, wherein, after the adjustment to alkaline pH in step v), the aqueous solution is stirred at room temperature for at least 1 hour.

7. A process for preparing a biocomposite of hydroxyapatite and calcium phosphate on graphene oxide sheets, the process comprising the steps of:
   a) providing a first supersatured SBF solution having pH of about 6.5,
   b) soaking graphene oxide sheets into said first supersatured SBF solution for a period of 65 to 85 hours,
   c) providing a second supersatured SBF solution having pH of about 6.0,
   d) soaking graphene oxide sheets obtained from step b) into said second supersatured SBF solution for a period of 40 to 60 hours, and
   e) rinsing with water and drying the biocomposite.

8. The process of claim 7, wherein both said first supersatured SBF solution and said second supersatured SBF solution are at a temperature of 30 to 40° C.

9. A biocomposite of hydroxyapatite and calcium phosphate on graphene oxide sheets obtained by the process of claim 1 or claim 7.

10. The biocomposite of claim 9 as obtainable by a process comprising the steps of:
    i) providing and sonicating an aqueous solution of graphene oxide to exfoliate graphene oxide sheets,
    ii) providing an aqueous solution of a Calcium salt selected from nitrate, sulphate, hydrogen sulphate, carbonate, chloride, nitride, and combinations thereof,
    iii) adding the aqueous solution of step ii) to the aqueous solution of step i),
    iv) providing an aqueous solution of a phosphorus salt selected from dihydrogen phosphate, hydrogen phosphate, phosphate, dihydrogen phosphite, hydrogen phosphite, phosphite, and combinations thereof, and
    v) adding the aqueous solution of step iv) to aqueous solution obtained in step iii), and gelating by adjusting to alkaline pH, thus obtaining the biocomposite,
    wherein said hydroxyapatite is in the form of spindle-like nanocrystals intercalated among graphene oxide sheets.

11. The biocomposite of claim 10, wherein in the spindle-like nanocrystals of hydroxyapatite, the ratio between calcium and phosphorus is 1.60 to 1.70.

12. The biocomposite of claim 9, having an X-ray diffraction pattern comprising the following peaks (2θ values): 25.9°, 28.9°, 31.8°, 39.8°, 46.7°, 49.5° and 53.2°.

13. The biocomposite of claim 12, having an X-ray diffraction pattern further comprising the following peaks (2θ values): 21.2°, 23.2° and 34.5°.

14. The biocomposite of claim 9 as obtainable by a process comprising the steps of:

a) providing a first supersatured SBF solution having pH of about 6.5,
b) soaking graphene oxide sheets into said first supersatured SBF solution for a period of 65 to 85 hours,
c) providing a second supersatured SBF solution having pH of about 6.0,
d) soaking graphene oxide sheets obtained from step b) into said second supersatured SBF solution for a period of 40 to 60 hours, and
e) rinsing with water and drying the biocomposite, wherein said calcium phosphate is amorphous calcium phosphate.

* * * * *